US 10,118,130 B2

(12) United States Patent
Swett

(10) Patent No.: US 10,118,130 B2
(45) Date of Patent: Nov. 6, 2018

(54) TWO-DIMENSIONAL MEMBRANE STRUCTURES HAVING FLOW PASSAGES

(71) Applicant: Lockheed Martin Corporation, Bethesda, MD (US)

(72) Inventor: Jacob Louis Swett, Redwood City, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 177 days.

(21) Appl. No.: 15/099,420

(22) Filed: Apr. 14, 2016

(65) Prior Publication Data

US 2017/0296973 A1    Oct. 19, 2017

(51) Int. Cl.
*B01D 63/08* (2006.01)

(52) U.S. Cl.
CPC ......... *B01D 63/087* (2013.01); *B01D 63/081* (2013.01)

(58) Field of Classification Search
None
See application file for complete search history.

(56) References Cited

U.S. PATENT DOCUMENTS

| | | |
|---|---|---|
| 2,187,417 A | 1/1940 | Doble |
| 3,024,153 A | 3/1962 | Kennedy |
| 3,303,085 A | 2/1967 | Price et al. |
| 3,501,831 A | 3/1970 | Gordon |
| 3,593,854 A | 7/1971 | Swank |
| 3,692,059 A | 9/1972 | Ice, Jr. |
| 3,701,433 A | 10/1972 | Krakauer et al. |
| 3,802,972 A | 4/1974 | Fleischer et al. |
| 4,073,732 A | 2/1978 | Lauer et al. |
| 4,159,954 A | 7/1979 | Gangemi |
| 4,162,220 A | 7/1979 | Servas |
| 4,277,344 A | 7/1981 | Cadotte |
| 4,303,530 A | 12/1981 | Shah et al. |

(Continued)

FOREIGN PATENT DOCUMENTS

| | | |
|---|---|---|
| CA | 2037988 | 9/1992 |
| CA | 2411935 | 12/2002 |

(Continued)

OTHER PUBLICATIONS

Barreiro et al. "Understanding the catalyst-free transformation of amorphous carbon into graphene by current-induced annealing," Scientific Reports, 3 (Article 1115): 1-6 (Jan. 2013).

(Continued)

*Primary Examiner* — Chester T Barry
(74) *Attorney, Agent, or Firm* — Foley & Lardner LLP

(57) ABSTRACT

A two-dimensional membrane layered structure may include a support substrate layer having a plurality of substrate passages configured to allow fluid to flow therethrough, a two-dimensional membrane layer disposed on an upper surface of the support substrate layer, and a plurality of flow passages disposed between the support substrate layer and the two-dimensional membrane layer. The two-dimensional membrane layer may have a plurality of pores configured to allow fluid to flow therethrough. The plurality of pores may comprise a first portion of pores that overlap with the plurality of substrate passages and a second portion of pores that do not overlap with the plurality of substrate passages. The plurality of flow passages may be configured to allow fluid to flow through the second portion of pores to the plurality of substrate passages.

15 Claims, 4 Drawing Sheets

(56) References Cited

U.S. PATENT DOCUMENTS

| | | |
|---|---|---|
| 4,743,371 A | 5/1988 | Servas et al. |
| 4,855,058 A | 8/1989 | Holland et al. |
| 4,880,440 A | 11/1989 | Perrin |
| 4,889,626 A | 12/1989 | Browne |
| 4,891,134 A | 1/1990 | Vcelka |
| 4,925,560 A | 5/1990 | Sorrick |
| 4,935,207 A | 6/1990 | Stanbro et al. |
| 4,976,858 A | 12/1990 | Kadoya |
| 5,052,444 A | 10/1991 | Messerly et al. |
| 5,080,770 A | 1/1992 | Culkin |
| 5,082,476 A | 1/1992 | Kahlbaugh et al. |
| 5,156,628 A | 10/1992 | Kranz |
| 5,182,111 A | 1/1993 | Aebischer et al. |
| 5,185,086 A | 2/1993 | Kaali et al. |
| 5,201,767 A | 4/1993 | Caldarise et al. |
| 5,244,981 A | 9/1993 | Seidner et al. |
| 5,314,492 A | 5/1994 | Hamilton et al. |
| 5,314,960 A | 5/1994 | Spinelli et al. |
| 5,314,961 A | 5/1994 | Anton et al. |
| 5,331,067 A | 7/1994 | Seidner et al. |
| 5,344,454 A | 9/1994 | Clarke et al. |
| 5,371,147 A | 12/1994 | Spinelli et al. |
| 5,425,858 A | 6/1995 | Farmer |
| 5,480,449 A | 1/1996 | Hamilton et al. |
| 5,514,181 A | 5/1996 | Light et al. |
| 5,516,522 A | 5/1996 | Peyman et al. |
| 5,549,697 A | 8/1996 | Caldarise |
| 5,562,944 A | 10/1996 | Kafrawy |
| 5,565,210 A | 10/1996 | Rosenthal et al. |
| 5,580,530 A | 12/1996 | Kowatsch et al. |
| 5,595,621 A | 1/1997 | Light et al. |
| 5,636,437 A | 6/1997 | Kaschmitter et al. |
| 5,639,275 A | 6/1997 | Baetge et al. |
| 5,641,323 A | 6/1997 | Caldarise |
| 5,658,334 A | 8/1997 | Caldarise et al. |
| 5,662,158 A | 9/1997 | Caldarise |
| 5,665,118 A | 9/1997 | LaSalle et al. |
| 5,671,897 A | 9/1997 | Ogg et al. |
| 5,679,232 A | 10/1997 | Fedor et al. |
| 5,679,249 A | 10/1997 | Fendya et al. |
| 5,687,788 A | 11/1997 | Caldarise et al. |
| 5,700,477 A | 12/1997 | Rosenthal et al. |
| 5,713,410 A | 2/1998 | LaSalle et al. |
| 5,716,412 A | 2/1998 | DeCarlo et al. |
| 5,716,414 A | 2/1998 | Caldarise |
| 5,725,586 A | 3/1998 | Sommerich |
| 5,731,360 A | 3/1998 | Pekala et al. |
| 5,733,503 A | 3/1998 | Kowatsch et al. |
| 5,746,272 A | 5/1998 | Mastrorio et al. |
| 5,782,286 A | 7/1998 | Sommerich |
| 5,782,289 A | 7/1998 | Mastrorio et al. |
| 5,788,916 A | 8/1998 | Caldarise |
| 5,800,828 A | 9/1998 | Dionne et al. |
| 5,808,312 A | 9/1998 | Fukuda |
| 5,868,727 A | 2/1999 | Barr et al. |
| 5,897,592 A | 4/1999 | Caldarise et al. |
| 5,902,762 A | 5/1999 | Mercuri et al. |
| 5,906,234 A | 5/1999 | Mastrorio et al. |
| 5,910,172 A | 6/1999 | Penenberg |
| 5,910,173 A | 6/1999 | DeCarlo et al. |
| 5,913,998 A | 6/1999 | Butler et al. |
| 5,922,304 A | 7/1999 | Unger |
| 5,925,247 A | 7/1999 | Huebbel |
| 5,932,185 A | 8/1999 | Pekala et al. |
| 5,935,084 A | 8/1999 | Southworth |
| 5,935,172 A | 8/1999 | Ochoa et al. |
| 5,954,937 A | 9/1999 | Farmer |
| 5,974,973 A | 11/1999 | Tittgemeyer |
| 5,976,555 A | 11/1999 | Liu et al. |
| 5,980,718 A | 11/1999 | Van Konynenburg et al. |
| 6,008,431 A | 12/1999 | Caldarise et al. |
| 6,013,080 A | 1/2000 | Khalili |
| 6,022,509 A | 2/2000 | Matthews et al. |
| 6,052,608 A | 4/2000 | Young et al. |
| 6,080,393 A | 6/2000 | Liu et al. |
| 6,093,209 A | 7/2000 | Sanders |
| 6,139,585 A | 10/2000 | Li |
| 6,152,882 A | 11/2000 | Prutchi |
| 6,156,323 A | 12/2000 | Verdicchio et al. |
| 6,193,956 B1 | 2/2001 | Liu et al. |
| 6,209,621 B1 | 4/2001 | Treacy |
| 6,213,124 B1 | 4/2001 | Butterworth |
| 6,228,123 B1 | 5/2001 | Dezzani |
| 6,264,699 B1 | 7/2001 | Noiles et al. |
| 6,292,704 B1 | 9/2001 | Malonek et al. |
| 6,309,532 B1 | 10/2001 | Tran et al. |
| 6,346,187 B1 | 2/2002 | Tran et al. |
| 6,375,014 B1 | 4/2002 | Garcera et al. |
| 6,426,214 B1 | 7/2002 | Butler et al. |
| 6,454,095 B1 | 9/2002 | Brisebois et al. |
| 6,455,115 B1 | 9/2002 | Demeyer |
| 6,461,622 B2 | 10/2002 | Liu et al. |
| 6,462,935 B1 | 10/2002 | Shiue et al. |
| 6,521,865 B1 | 2/2003 | Jones et al. |
| 6,532,386 B2 | 3/2003 | Sun et al. |
| 6,544,316 B2 | 4/2003 | Baker et al. |
| 6,580,598 B2 | 6/2003 | Shiue et al. |
| 6,654,229 B2 | 11/2003 | Yanagisawa et al. |
| 6,659,298 B2 | 12/2003 | Wong |
| 6,660,150 B2 | 12/2003 | Conlan et al. |
| 6,661,643 B2 | 12/2003 | Shiue et al. |
| 6,686,437 B2 | 2/2004 | Buchman et al. |
| 6,692,627 B1 | 2/2004 | Russell et al. |
| 6,695,880 B1 | 2/2004 | Roffman et al. |
| 6,699,684 B2 | 3/2004 | Ho et al. |
| 6,719,740 B2 | 4/2004 | Burnett et al. |
| 6,905,612 B2 | 6/2005 | Dorian et al. |
| 6,924,190 B2 | 8/2005 | Dennison |
| 7,014,829 B2 | 3/2006 | Yanagisawa et al. |
| 7,071,406 B2 | 7/2006 | Smalley et al. |
| 7,092,753 B2 | 8/2006 | Darvish et al. |
| 7,138,042 B2 | 11/2006 | Tran et al. |
| 7,171,263 B2 | 1/2007 | Darvish et al. |
| 7,175,783 B2 | 2/2007 | Curran |
| 7,179,419 B2 | 2/2007 | Lin et al. |
| 7,190,997 B1 | 3/2007 | Darvish et al. |
| 7,267,753 B2 | 9/2007 | Anex et al. |
| 7,306,768 B2 | 12/2007 | Chiga |
| 7,357,255 B2 | 4/2008 | Ginsberg et al. |
| 7,374,677 B2 | 5/2008 | McLaughlin et al. |
| 7,381,707 B2 | 6/2008 | Lin et al. |
| 7,382,601 B2 | 6/2008 | Yoshimitsu |
| 7,434,692 B2 | 10/2008 | Ginsberg et al. |
| 7,452,547 B2 | 11/2008 | Lambino et al. |
| 7,459,121 B2 | 12/2008 | Liang et al. |
| 7,460,907 B1 | 12/2008 | Darvish et al. |
| 7,476,222 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,505,250 B2 | 3/2009 | Cho et al. |
| 7,531,094 B2 | 5/2009 | McLaughlin et al. |
| 7,600,567 B2 | 10/2009 | Christopher et al. |
| 7,631,764 B2 | 12/2009 | Ginsberg et al. |
| 7,650,805 B2 | 1/2010 | Nauseda et al. |
| 7,674,477 B1 | 3/2010 | Schmid et al. |
| 7,706,128 B2 | 4/2010 | Bourcier |
| 7,761,809 B2 | 7/2010 | Bukovec et al. |
| 7,786,086 B2 | 8/2010 | Reches et al. |
| 7,866,475 B2 | 1/2011 | Doskoczynski et al. |
| 7,875,293 B2 | 1/2011 | Shults et al. |
| 7,935,331 B2 | 5/2011 | Lin |
| 7,935,416 B2 | 5/2011 | Yang et al. |
| 7,943,167 B2 | 5/2011 | Kulkarni et al. |
| 7,960,708 B2 | 6/2011 | Wolfe et al. |
| 7,998,246 B2 | 8/2011 | Liu et al. |
| 8,109,893 B2 | 2/2012 | Lande |
| 8,147,599 B2 | 4/2012 | McAlister |
| 8,262,943 B2 | 9/2012 | Meng et al. |
| 8,278,106 B2 | 10/2012 | Martinson et al. |
| 8,308,702 B2 | 11/2012 | Batchvarova et al. |
| 8,316,865 B2 | 11/2012 | Ochs et al. |
| 8,329,476 B2 | 12/2012 | Pitkanen et al. |

(56) References Cited

U.S. PATENT DOCUMENTS

| | | |
|---|---|---|
| 8,354,296 B2 | 1/2013 | Dimitrakopoulos et al. |
| 8,361,321 B2 | 1/2013 | Stetson et al. |
| 8,449,504 B2 | 5/2013 | Carter et al. |
| 8,471,562 B2 | 6/2013 | Knizhnik |
| 8,475,689 B2 | 7/2013 | Sun et al. |
| 8,506,807 B2 | 8/2013 | Lee et al. |
| 8,512,669 B2 | 8/2013 | Hauck |
| 8,513,324 B2 | 8/2013 | Scales et al. |
| 8,535,726 B2 | 9/2013 | Dai et al. |
| 8,592,291 B2 | 11/2013 | Shi et al. |
| 8,617,411 B2 | 12/2013 | Singh |
| 8,666,471 B2 | 3/2014 | Rogers et al. |
| 8,686,249 B1 | 4/2014 | Whitaker et al. |
| 8,697,230 B2 | 4/2014 | Ago et al. |
| 8,698,481 B2 | 4/2014 | Lieber et al. |
| 8,715,329 B2 | 5/2014 | Robinson et al. |
| 8,721,074 B2 | 5/2014 | Pugh et al. |
| 8,734,421 B2 | 5/2014 | Sun et al. |
| 8,744,567 B2 | 6/2014 | Fassih et al. |
| 8,751,015 B2 | 6/2014 | Frewin et al. |
| 8,753,468 B2 | 6/2014 | Caldwell et al. |
| 8,759,153 B2 | 6/2014 | Elian et al. |
| 8,808,257 B2 | 8/2014 | Pugh et al. |
| 8,828,211 B2 | 9/2014 | Garaj et al. |
| 8,840,552 B2 | 9/2014 | Brauker et al. |
| 8,857,983 B2 | 10/2014 | Pugh et al. |
| 8,861,821 B2 | 10/2014 | Osumi |
| 8,894,201 B2 | 11/2014 | Pugh et al. |
| 8,940,552 B2 | 1/2015 | Pugh et al. |
| 8,950,862 B2 | 2/2015 | Pugh et al. |
| 8,974,055 B2 | 3/2015 | Pugh et al. |
| 8,975,121 B2 | 3/2015 | Pugh et al. |
| 8,979,978 B2 | 3/2015 | Miller et al. |
| 8,986,932 B2 | 3/2015 | Turner et al. |
| 8,993,234 B2 | 3/2015 | Turner et al. |
| 8,993,327 B2 | 3/2015 | McKnight et al. |
| 9,014,639 B2 | 4/2015 | Pugh et al. |
| 9,017,937 B1 | 4/2015 | Turner et al. |
| 9,023,220 B2 | 5/2015 | Zurutuza Elorza et al. |
| 9,028,663 B2 | 5/2015 | Stetson et al. |
| 9,035,282 B2 | 5/2015 | Dimitrakopoulos et al. |
| 9,045,847 B2 | 6/2015 | Batchvarova et al. |
| 9,050,452 B2 | 6/2015 | Sun et al. |
| 9,052,533 B2 | 6/2015 | Pugh et al. |
| 9,056,282 B2 | 6/2015 | Miller et al. |
| 9,062,180 B2 | 6/2015 | Scales et al. |
| 9,067,811 B1 | 6/2015 | Bennett et al. |
| 9,070,615 B2 | 6/2015 | Elian et al. |
| 9,075,009 B2 | 7/2015 | Kim et al. |
| 9,080,267 B2 | 7/2015 | Batchvarova et al. |
| 9,095,823 B2 | 8/2015 | Fleming |
| 9,096,050 B2 | 8/2015 | Bedell et al. |
| 9,096,437 B2 | 8/2015 | Tour et al. |
| 9,102,111 B2 | 8/2015 | Pugh et al. |
| 9,108,158 B2 | 8/2015 | Yu et al. |
| 9,110,310 B2 | 8/2015 | Pugh et al. |
| 9,125,715 B2 | 9/2015 | Pugh et al. |
| 9,134,546 B2 | 9/2015 | Pugh et al. |
| 9,170,646 B2 | 10/2015 | Toner et al. |
| 9,185,486 B2 | 11/2015 | Pugh |
| 9,193,587 B2 | 11/2015 | Bennett |
| 9,195,075 B2 | 11/2015 | Pugh et al. |
| 9,225,375 B2 | 12/2015 | Pugh et al. |
| 9,388,048 B1 | 7/2016 | Zhou et al. |
| 9,425,709 B2 | 8/2016 | Hayashi et al. |
| 9,437,370 B2 | 9/2016 | Chen et al. |
| 9,463,421 B2 | 10/2016 | Fleming |
| 9,505,192 B2 | 11/2016 | Stoltenberg et al. |
| 9,567,224 B2 | 2/2017 | Bedworth |
| 9,572,918 B2 | 2/2017 | Bachmann et al. |
| 9,592,475 B2 | 3/2017 | Stoltenberg et al. |
| 9,610,546 B2 | 4/2017 | Sinton et al. |
| 9,708,640 B2 | 7/2017 | Wu et al. |
| 9,713,794 B2 | 7/2017 | Choi et al. |
| 9,742,001 B2 | 8/2017 | Zhamu et al. |
| 9,870,895 B2 | 1/2018 | Bedworth |
| 2001/0036556 A1 | 11/2001 | Jen |
| 2001/0047157 A1 | 11/2001 | Burnett et al. |
| 2001/0055597 A1 | 12/2001 | Liu et al. |
| 2002/0079004 A1 | 6/2002 | Sato et al. |
| 2002/0079054 A1 | 6/2002 | Nakatani |
| 2002/0104435 A1 | 8/2002 | Baker et al. |
| 2002/0115957 A1 | 8/2002 | Sun et al. |
| 2002/0117659 A1 | 8/2002 | Lieber et al. |
| 2002/0183682 A1 | 12/2002 | Darvish et al. |
| 2002/0183686 A1 | 12/2002 | Darvish et al. |
| 2003/0052354 A1 | 3/2003 | Dennison |
| 2003/0134281 A1 | 7/2003 | Evans |
| 2003/0138777 A1 | 7/2003 | Evans |
| 2003/0146221 A1 | 8/2003 | Lauer et al. |
| 2003/0159985 A1 | 8/2003 | Siwy et al. |
| 2004/0018583 A1 | 1/2004 | Ho et al. |
| 2004/0035787 A1 | 2/2004 | Tanga et al. |
| 2004/0061253 A1 | 4/2004 | Kleinmeyer et al. |
| 2004/0063097 A1 | 4/2004 | Evans |
| 2004/0099324 A1 | 5/2004 | Fraser et al. |
| 2004/0111968 A1 | 6/2004 | Day et al. |
| 2004/0112865 A1 | 6/2004 | McCullough et al. |
| 2004/0121488 A1 | 6/2004 | Chang et al. |
| 2004/0142463 A1 | 7/2004 | Walker et al. |
| 2004/0185730 A1 | 9/2004 | Lambino et al. |
| 2004/0193043 A1 | 9/2004 | Duchon et al. |
| 2004/0199243 A1 | 10/2004 | Yodfat |
| 2004/0208796 A1 | 10/2004 | Chiga |
| 2004/0217036 A1 | 11/2004 | Ginsberg et al. |
| 2004/0241214 A1 | 12/2004 | Kirkwood et al. |
| 2004/0251136 A1 | 12/2004 | Lean et al. |
| 2005/0004508 A1 | 1/2005 | Sun et al. |
| 2005/0004509 A1 | 1/2005 | Sun et al. |
| 2005/0004550 A1 | 1/2005 | Sun et al. |
| 2005/0010161 A1 | 1/2005 | Sun et al. |
| 2005/0010192 A1 | 1/2005 | Sun et al. |
| 2005/0015042 A1 | 1/2005 | Sun et al. |
| 2005/0053563 A1 | 3/2005 | Manissier et al. |
| 2005/0112078 A1 | 5/2005 | Boddupalli et al. |
| 2005/0126966 A1 | 6/2005 | Tanida et al. |
| 2005/0129633 A1 | 6/2005 | Lin |
| 2005/0148996 A1 | 7/2005 | Sun et al. |
| 2005/0170089 A1 | 8/2005 | Lashmore et al. |
| 2005/0189673 A1 | 9/2005 | Klug et al. |
| 2005/0226834 A1 | 10/2005 | Lambino et al. |
| 2005/0238730 A1 | 10/2005 | Le Fur et al. |
| 2006/0005381 A1 | 1/2006 | Nishi et al. |
| 2006/0036332 A1 | 2/2006 | Jennings |
| 2006/0073370 A1 | 4/2006 | Krusic et al. |
| 2006/0093885 A1 | 5/2006 | Krusic et al. |
| 2006/0121279 A1 | 6/2006 | Petrik |
| 2006/0151382 A1 | 7/2006 | Petrik |
| 2006/0166347 A1 | 7/2006 | Faulstich et al. |
| 2006/0180604 A1 | 8/2006 | Ginsberg et al. |
| 2006/0222701 A1 | 10/2006 | Kulkarni et al. |
| 2006/0253078 A1 | 11/2006 | Wu et al. |
| 2007/0004640 A1 | 1/2007 | Lin et al. |
| 2007/0032054 A1 | 2/2007 | Ramaswamy et al. |
| 2007/0056894 A1 | 3/2007 | Connors, Jr. |
| 2007/0060862 A1 | 3/2007 | Sun et al. |
| 2007/0062856 A1 | 3/2007 | Pahl et al. |
| 2007/0099813 A1 | 5/2007 | Luizzi et al. |
| 2007/0131646 A1 | 6/2007 | Donnelly et al. |
| 2007/0284279 A1 | 12/2007 | Doskoczynski et al. |
| 2008/0017564 A1 | 1/2008 | Hammond |
| 2008/0035484 A1 | 2/2008 | Wu et al. |
| 2008/0035541 A1 | 2/2008 | Franzreb et al. |
| 2008/0045877 A1 | 2/2008 | Levin et al. |
| 2008/0061477 A1 | 3/2008 | Capizzo |
| 2008/0063585 A1 | 3/2008 | Smalley et al. |
| 2008/0081323 A1 | 4/2008 | Keeley et al. |
| 2008/0081362 A1 | 4/2008 | Keeley et al. |
| 2008/0149561 A1 | 6/2008 | Chu et al. |
| 2008/0156648 A1 | 7/2008 | Dudziak et al. |
| 2008/0170982 A1 | 7/2008 | Zhang et al. |
| 2008/0185293 A1 | 8/2008 | Klose et al. |
| 2008/0188836 A1 | 8/2008 | Weber et al. |
| 2008/0190508 A1 | 8/2008 | Booth et al. |

(56) References Cited

U.S. PATENT DOCUMENTS

| | | |
|---|---|---|
| 2008/0241085 A1 | 10/2008 | Lin et al. |
| 2008/0268016 A1 | 10/2008 | Fang et al. |
| 2008/0290020 A1 | 11/2008 | Marand et al. |
| 2008/0290111 A1 | 11/2008 | Ginsberg et al. |
| 2009/0023572 A1 | 1/2009 | Backes et al. |
| 2009/0032475 A1 | 2/2009 | Ferrer et al. |
| 2009/0039019 A1 | 2/2009 | Raman |
| 2009/0048685 A1 | 2/2009 | Frigstad et al. |
| 2009/0075371 A1 | 3/2009 | Keeley et al. |
| 2009/0078640 A1 | 3/2009 | Chu et al. |
| 2009/0087395 A1 | 4/2009 | Lin et al. |
| 2009/0117335 A1 | 5/2009 | Iyoda et al. |
| 2009/0148495 A1 | 6/2009 | Hammer et al. |
| 2009/0176159 A1 | 7/2009 | Zhamu et al. |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0283475 A1 | 11/2009 | Hylton et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209330 A1 | 8/2010 | Golzhauser et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1 | 5/2011 | Heinrich |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0132834 A1 | 6/2011 | Tomioka et al. |
| 2011/0139707 A1 | 6/2011 | Siwy et al. |
| 2011/0152795 A1 | 6/2011 | Aledo et al. |
| 2011/0189440 A1 | 8/2011 | Appleby et al. |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0000845 A1 | 1/2012 | Park et al. |
| 2012/0031833 A1 | 2/2012 | Ho et al. |
| 2012/0048804 A1 | 3/2012 | Stetson et al. |
| 2012/0115243 A1 | 5/2012 | Pitkanen et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0219203 A1 | 8/2012 | Adachi |
| 2012/0220053 A1 | 8/2012 | Lee et al. |
| 2012/0234453 A1 | 9/2012 | Pugh et al. |
| 2012/0234679 A1 | 9/2012 | Garaj et al. |
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0298396 A1 | 11/2012 | Hong et al. |
| 2012/0301707 A1 | 11/2012 | Kinloch et al. |
| 2013/0015136 A1 | 1/2013 | Bennett |
| 2013/0034760 A1 | 2/2013 | Otts et al. |
| 2013/0045523 A1 | 2/2013 | Leach et al. |
| 2013/0056367 A1 | 3/2013 | Martinez et al. |
| 2013/0071941 A1 | 3/2013 | Miller |
| 2013/0096292 A1 | 4/2013 | Brahmasandra et al. |
| 2013/0100436 A1 | 4/2013 | Jackson et al. |
| 2013/0105417 A1 | 5/2013 | Stetson et al. |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |
| 2013/0146221 A1 | 6/2013 | Kolmakov et al. |
| 2013/0146480 A1 | 6/2013 | Garaj et al. |
| 2013/0152386 A1 | 6/2013 | Pandojirao-S et al. |
| 2013/0174968 A1 | 7/2013 | Vlassiouk et al. |
| 2013/0174978 A1 | 7/2013 | Pugh et al. |
| 2013/0176030 A1 | 7/2013 | Simon |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1 | 9/2013 | Bedworth |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |
| 2013/0270188 A1 | 10/2013 | Karnik et al. |
| 2013/0273288 A1 | 10/2013 | Luo et al. |
| 2013/0277305 A1 | 10/2013 | Stetson et al. |
| 2013/0284665 A1 | 10/2013 | Lee et al. |
| 2013/0295150 A1 | 11/2013 | Chantalat et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0335092 A1 | 12/2013 | Wu |
| 2013/0338611 A1 | 12/2013 | Pugh et al. |
| 2013/0338744 A1 | 12/2013 | Frewin et al. |

(56) References Cited

U.S. PATENT DOCUMENTS

| | | |
|---|---|---|
| 2014/0002788 A1 | 1/2014 | Otts et al. |
| 2014/0005514 A1 | 1/2014 | Pugh et al. |
| 2014/0015160 A1 | 1/2014 | Kung et al. |
| 2014/0017322 A1 | 1/2014 | Dai et al. |
| 2014/0030482 A1 | 1/2014 | Miller et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |
| 2014/0174927 A1 | 6/2014 | Bashir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0253131 A1 | 9/2014 | Liu et al. |
| 2014/0257348 A1 | 9/2014 | Priewe et al. |
| 2014/0257515 A1 | 9/2014 | So et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1 | 9/2014 | Stoltenberg et al. |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1 | 9/2014 | Stoltenberg et al. |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0311967 A1 | 10/2014 | Grossman et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0346631 A1 | 11/2014 | Karim et al. |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0053627 A1 | 2/2015 | Silin et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0137817 A1 | 5/2015 | Wilson et al. |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0170788 A1 | 6/2015 | Miller et al. |
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |
| 2015/0221474 A1 | 8/2015 | Bedworth |
| 2015/0231557 A1 | 8/2015 | Miller et al. |
| 2015/0231577 A1 | 8/2015 | Nair et al. |
| 2015/0247178 A1 | 9/2015 | Mountcastle et al. |
| 2015/0258254 A1 | 9/2015 | Simon et al. |
| 2015/0258498 A1 | 9/2015 | Simon et al. |
| 2015/0258502 A1 | 9/2015 | Turowski |
| 2015/0258503 A1 | 9/2015 | Sinton et al. |
| 2015/0258506 A1 | 9/2015 | Mi et al. |
| 2015/0258525 A1 | 9/2015 | Westman et al. |
| 2015/0268150 A1 | 9/2015 | Newkirk et al. |
| 2015/0272834 A1 | 10/2015 | Sun et al. |
| 2015/0272896 A1 | 10/2015 | Sun et al. |
| 2015/0273401 A1 | 10/2015 | Miller et al. |
| 2015/0309337 A1 | 10/2015 | Flitsch et al. |
| 2015/0321147 A1 | 11/2015 | Fleming et al. |
| 2015/0321149 A1 | 11/2015 | McGinnis |
| 2015/0323811 A1 | 11/2015 | Flitsch et al. |
| 2015/0336202 A1 | 11/2015 | Bedworth et al. |
| 2015/0342900 A1 | 12/2015 | Putnins |
| 2015/0346382 A1 | 12/2015 | Bliven et al. |
| 2015/0351887 A1 | 12/2015 | Peters |
| 2015/0359742 A1 | 12/2015 | Fassih et al. |
| 2015/0378176 A1 | 12/2015 | Flitsch et al. |
| 2016/0009049 A1 | 1/2016 | Stoltenberg et al. |
| 2016/0038885 A1 | 2/2016 | Hogen-Esch et al. |
| 2016/0043384 A1 | 2/2016 | Zhamu et al. |
| 2016/0058932 A1 | 3/2016 | Stetson et al. |
| 2016/0059190 A1 | 3/2016 | Yoo et al. |
| 2016/0067390 A1 | 3/2016 | Simon et al. |
| 2016/0074814 A1 | 3/2016 | Park et al. |
| 2016/0074815 A1 | 3/2016 | Sinton et al. |
| 2016/0084008 A1 | 3/2016 | Faircloth et al. |
| 2016/0084981 A1 | 3/2016 | Kayano et al. |
| 2016/0116237 A1 | 4/2016 | Alsadah et al. |
| 2016/0256805 A1 | 9/2016 | Grein et al. |
| 2016/0272499 A1 | 9/2016 | Zurutuza Elorza et al. |
| 2016/0282326 A1 | 9/2016 | Waduge et al. |
| 2016/0284811 A1 | 9/2016 | Yu et al. |
| 2016/0339160 A1 | 11/2016 | Bedworth et al. |
| 2017/0000937 A1 | 1/2017 | Gottschalk |
| 2017/0032962 A1 | 2/2017 | Zurutuza Elorza et al. |
| 2017/0035943 A1 | 2/2017 | Simon et al. |
| 2017/0036916 A1 | 2/2017 | Bedworth et al. |
| 2017/0037356 A1 | 2/2017 | Simon et al. |
| 2017/0057812 A1 | 3/2017 | Zurutuza Elorza et al. |
| 2017/0065939 A1 | 3/2017 | Kim et al. |
| 2017/0144107 A1 | 5/2017 | Garaj et al. |
| 2017/0202885 A1 | 7/2017 | Agulnick |

(56) References Cited

U.S. PATENT DOCUMENTS

| | | | |
|---|---|---|---|
| 2017/0216923 A1 | 8/2017 | Babenko et al. |
| 2017/0217777 A1 | 8/2017 | Hong et al. |
| 2017/0239623 A1 | 8/2017 | Stoltenberg et al. |
| 2017/0296706 A1 | 10/2017 | Simon et al. |
| 2017/0296972 A1 | 10/2017 | Sinton et al. |
| 2017/0296976 A1 | 10/2017 | Liu et al. |
| 2017/0296979 A1 | 10/2017 | Swett et al. |
| 2018/0207591 A1 | 7/2018 | Yu et al. |

FOREIGN PATENT DOCUMENTS

| | | |
|---|---|---|
| CN | 1128501 A | 8/1996 |
| CN | 101108194 A | 1/2008 |
| CN | 101243544 | 8/2008 |
| CN | 101428198 A | 5/2009 |
| CN | 101489653 A | 7/2009 |
| CN | 101996853 A | 3/2011 |
| CN | 102242062 A | 11/2011 |
| CN | 102344132 | 2/2012 |
| CN | 102423272 | 4/2012 |
| CN | 102592720 A | 7/2012 |
| CN | 101996853 B | 8/2012 |
| CN | 102637584 A | 8/2012 |
| CN | 103153441 | 6/2013 |
| CN | 103182249 A | 7/2013 |
| CN | 203235358 | 10/2013 |
| CN | 103480281 | 1/2014 |
| CN | 103585891 | 2/2014 |
| CN | 103603706 A | 2/2014 |
| DE | 19536560 | 3/1997 |
| DE | 10 2005 049 388 A1 | 4/2007 |
| EP | 0 364 628 A1 | 4/1990 |
| EP | 1 034 251 | 1/2004 |
| EP | 1 777 250 A1 | 4/2007 |
| EP | 1 872 812 | 1/2008 |
| EP | 2 060 286 | 5/2009 |
| EP | 2 107 120 A1 | 10/2009 |
| EP | 2 230 511 A1 | 9/2010 |
| EP | 1 603 609 | 5/2011 |
| EP | 2 354 272 | 8/2011 |
| EP | 2 450 096 | 5/2012 |
| EP | 2 489 520 | 8/2012 |
| EP | 2 511 002 | 10/2012 |
| EP | 2 586 473 | 5/2013 |
| EP | 2 679 540 | 1/2014 |
| EP | 2 937 313 | 10/2015 |
| EP | 3 070 053 | 9/2016 |
| EP | 3 084 398 | 10/2016 |
| EP | 1 538 2430.5 | 3/2017 |
| EP | 3 135 631 | 3/2017 |
| JP | 59-102111 | 7/1984 |
| JP | 10-510471 | 5/1995 |
| JP | 7504120 | 5/1995 |
| JP | 2001-232158 | 8/2001 |
| JP | 2002-126510 | 5/2002 |
| JP | 2004-179014 | 6/2004 |
| JP | 2005-126966 | 5/2005 |
| JP | 2006-188393 | 7/2006 |
| JP | 2009-291777 | 12/2009 |
| JP | 2011-168448 A | 9/2011 |
| JP | 2011-241479 | 12/2011 |
| JP | 2012-500708 | 1/2012 |
| JP | 2004-202480 | 7/2014 |
| JP | 2015-503405 | 2/2015 |
| JP | 2016-175828 | 10/2016 |
| KR | 1020110084110 | 7/2011 |
| KR | 10-2012-0022164 A | 3/2012 |
| KR | 1020120022164 A | 3/2012 |
| KR | 1020140002570 | 1/2014 |
| WO | WO-93/33901 | 3/1993 |
| WO | WO-93/12859 | 8/1993 |
| WO | WO-95/00231 | 1/1995 |
| WO | WO-97/12664 A1 | 4/1997 |
| WO | WO-98/30501 A2 | 7/1998 |
| WO | WO-00/70012 | 11/2000 |
| WO | WO-02/055539 A1 | 7/2002 |
| WO | WO-2013/115762 | 8/2003 |
| WO | WO-2004/009840 A1 | 1/2004 |
| WO | WO-2004/082733 | 9/2004 |
| WO | WO-2005/047857 A2 | 5/2005 |
| WO | WO-2007/103411 A2 | 9/2007 |
| WO | WO-2007/140252 A1 | 12/2007 |
| WO | WO-2008/008533 | 1/2008 |
| WO | WO-2009/129984 A1 | 10/2009 |
| WO | WO-2010/006080 | 1/2010 |
| WO | WO-2010/115904 A1 | 10/2010 |
| WO | WO-2011/019686 A1 | 2/2011 |
| WO | WO-2011/046706 A1 | 4/2011 |
| WO | WO-2011/001674 | 6/2011 |
| WO | WO-2011/063458 A1 | 6/2011 |
| WO | WO-2011/075158 | 6/2011 |
| WO | WO-2011/094204 A2 | 8/2011 |
| WO | WO-2011/100458 A2 | 8/2011 |
| WO | WO-2011/138689 A2 | 11/2011 |
| WO | WO-2012/006657 A1 | 1/2012 |
| WO | WO-2012/021801 A2 | 2/2012 |
| WO | WO-2012/027148 A1 | 3/2012 |
| WO | WO-2012/028695 | 3/2012 |
| WO | WO-2012/030368 A1 | 3/2012 |
| WO | WO-2012/125770 | 9/2012 |
| WO | WO-2012/138671 A2 | 10/2012 |
| WO | WO-2012/142852 A1 | 10/2012 |
| WO | WO-2013/016445 A1 | 1/2013 |
| WO | WO-2013/048063 A1 | 4/2013 |
| WO | WO-2013/138137 A1 | 9/2013 |
| WO | WO-2013/138698 A1 | 9/2013 |
| WO | WO-2013/151799 | 10/2013 |
| WO | WO-2013/152179 A1 | 10/2013 |
| WO | WO-2014/084856 | 6/2014 |
| WO | WO-2014/084861 A1 | 6/2014 |
| WO | WO-2014/168629 A1 | 10/2014 |
| WO | WO-2015/030698 A1 | 3/2015 |
| WO | WO-2015/110277 | 7/2015 |
| WO | WO-2015/138736 A1 | 9/2015 |
| WO | WO-2015/138752 A1 | 9/2015 |
| WO | WO-2015/138771 A1 | 9/2015 |
| WO | WO-2015/197217 | 12/2015 |
| WO | WO-2016/102003 | 6/2016 |

OTHER PUBLICATIONS

Botari et al., "Graphene healing mechanisms: A theoretical investigation," Carbon, 99: 302-309 (Apr. 2016) (published online Dec. 2015).

Chen et al., "Defect Scattering in Graphene," Physical Review Letters, 102: 236805-1-236805-4 (Jun. 2009).

Chen et al., "Self-healing of defected graphene," Applied Physics Letters, 102(10): 103107-1-103107-5 (Mar. 2013).

Cheng et al., "Ion Transport in Complex Layered Graphene-Based Membranes with Tuneable Interlayer Spacing," Science Advances, 2(2): e1501272 (9 pages) (Feb. 2016).

Crock et al., "Polymer Nanocomposites with Graphene-Based Hierarchical Fillers as Materials for Multifunctional Water Treatment Membranes," Water Research, 47(12): 3984-3996 (Aug. 2013) (published online Mar. 2013).

Han et al., "Ultrathin Graphene Nanofiltration Membrane for Water Purification," Advanced Functional Materials, 23(29): 3693-3700 (Aug. 2013).

International Search Report and Written Opinion in PCT/US2016/027583 dated Jan. 13, 2017.

Written Opinion in PCT/US2016/027590 dated Jan. 6, 2017.

International Search Report and Written Opinion in PCT/US2016/027594 dated Jan. 13, 2017.

International Search Report and Written Opinion in PCT/US2016/027628 dated Jan. 9, 2017.

International Search Report and Written Opinion in PCT/US2016/027631 dated Jan. 13, 2017.

International Search Report and Written Opinion in PCT/US2016/027632 dated Jan. 9, 2017.

Written Opinion in PCT/US2016/052010 dated Dec. 20, 2016.

(56) References Cited

OTHER PUBLICATIONS

International Search Report in PCT/US2016/027629 dated Dec. 8, 2016.
International Search Report in PCT/US2016/052007 dated Dec. 27, 2016.
Kjeldsen, T., "Yeast secretory expression of insulin precursors," Appl Microbiol Biotechnol, 54: 277-286 (May 2000).
Lin et al., "A Direct and Polymer-Free Method for Transferring Graphene Grown by Chemical Vapor Deposition to Any Substrate," ACSNANO, 8(2): 1784-1791 (Jan. 2014).
Liu et al. "Synthesis of high-quality monolayer and bilayer graphene on copper using chemical vapor deposition," Carbon, 49(13): 4122-4130 (Nov. 2011) (published online May 2011).
O'Hern et al., "Nanofiltration across defect-sealed nanoporous monolayer graphene," Nano Letters, 15(5): 3254-3260 (Apr. 2015).
U.S. Corrected Notice of Allowance in U.S. Appl. No. 13/480,569 dated May 26, 2015.
U.S. Notice of Allowance for U.S. Appl. No. 14/610,770 dated Apr. 25, 2016.
U.S. Notice of Allowance in U.S. Appl. No. 14/819,273 dated Dec. 14, 2016.
U.S. Notice of Allowance in U.S. Appl. No. 13/480,569 dated Feb. 27, 2015.
U.S. Office Action in U.S. Appl. No. 13/480,569 dated Jul. 30, 2014.
U.S. Office Action in U.S. Appl. No. 14/856,471 dated Dec. 1, 2016.
U.S. Restriction Requirement in U.S. Appl. No. 14/193,007 dated Jul. 17, 2015.
Wang et al., "Graphene Oxide Membranes with Tunable Permeability due to Embedded Carbon Dots," Chemical Communications, 50(86): 13089-13092 (Nov. 2014) (published online Sep. 2014).
Xu et al., "Graphene Oxide-TiO$_2$ Composite Filtration Membranes and their Potential Application for Water Purification," Carbon, 62: 465-471 (Oct. 2013) (published online Jun. 2013).
Zhao et al., "A glucose-responsive controlled release of insulin system based on enzyme multilayers-coated mesoporous silica particles," Chem. Commun., 47: 9459-9461 (Jun. 2011).
CN Office Action in Chinese Application No. 201580006829.5 dated Aug. 1, 2017. (English translation) (5 pages).
EP Office Action for European Application No. 15743307.9 dated Aug. 8, 2017. (17 pages).
European Search Report dated Aug. 28, 2017 from related EP application 15743750.0. (7 pages).
International Search Report and Written Opinion dated Aug. 14, 2017 from related PCT application PCT/US2017/031537. (12 pages).
Jiang, L. et al., Design of advanced porous grapheme materials: from grapheme nanomesh to 3D architectures. Nanoscale, Oct. 16, 2013, vol. 6, pp. 1922-1945.
JP Office Action in Japanese Application No. 2015-503405 dated Jun. 28, 2017. (English translation) (6 pages).
JP Office Action in Japanese Application No. 2015-549508 dated Jun. 27, 2017. (English translation) (7 pages).
Li, R.H. "Materials for immunoisolated cell transplantation". Adv. Drug Deliv. Rev. 33, 87-109 (1998). (23 pages).
Schweitzer, Handbook of Separation Techniques for Chemical Engineers, 1979, McGraw-Hill Book Company, pp. 2-5 to 2-8.
Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (Jan. 4, 2010), pp. 127-149.
U.S. Notice of Allowance in U.S. Appl. No. 14/193,007 dated Sep. 6, 2017. (9 pages).
U.S. Notice of Allowance in U.S. Appl. No. 14/656,580 dated Sep. 5, 2017. (8 pages).
U.S. Office Action for U.S. Appl. No. 14/609,325 dated Aug. 25, 2017. (7 pages).
U.S. Office Action for U.S. Appl. No. 15/099,193 dated Jul. 19, 2017. (13 pages).
U.S. Office Action for U.S. Appl. No. 15/289,944 dated Jul. 13, 2017. (18 pages).
U.S. Office Action for U.S. Appl. No. 15/332,982 dated Aug. 18, 2017. (9 pages).
AE Search and Examination Report for United Arab Emirates Application No. P186/13 dated Oct. 4, 2016.
Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc., "Filmtec Nanofiltration Membrane Elements", Retrieved from appliedmembranes.com/nanofiltration_elements.htm, accessed Apr. 28, 2015 (2 Pages).
Aso et al., "Comparison of serum high-molecular weight (HMW) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
AU Examination Report for Australian Patent Application No. 2013235234, dated Jan. 13, 2017, 4 pages.
AU Examination Report for Australian Patent Application No. 2013363283, dated Jun. 20, 2017, 4 pages.
AU Notice of Acceptance for Australian Application No. 2011293742 dated Jan. 13, 2016.
Axelsson et al., "Acute hyperglycemia induces rapid, reversible increases in glomerular permeability in nondiabetic rats," Am. J. Physiol. Renal Physiol. 298(6): F1306-F1312 (Jun. 2010) (available online Mar. 17, 2010).
Bains et al., "Novel lectins from rhizomes of two Acorus species with mitogenic activity and inhibitory potential towards murine cancer cell lines," Int'l Immunopharmacol. 5(9): 1470-1478 (Aug. 2005) (available online May 12, 2005).
Baker, "Membrane Technology and Applications", Membrane Technology and Applications; Apr. 14, 2004; pp. 92-94.
Barreiro et al. "Transport properties of graphene in the high-current limit." Physical review letters 103.7 (2009): 076601.
Bazargani et al. "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Bieri et al. "Two-dimensional Polymer Formation on Surfaces: Insight into the Roles of Precursor Mobility and Reactivity" JACS, 2010, vol. 132, pp. 16669-16676.
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Chu Ju, et al. "Modern Biotechnology" East China University of Technology Press, (Sep. 2007), vol. 1; pp. 306-307, ISBN 978-7-5628-2116-8.
Clochard, "Track-Etched Polymer Membranes," Laboratory of Irradiated Solids, Ecole Polytechnique, retrieved from http://www.lsi.polytechnique.fr/home/research/physics-and-chemistry-of-nano-objects/trac . . . , Accessed Jul. 30, 2015 (2 pages).
CN Notification of Grant for Chinese Application No. 201180049184.5 dated Jun. 6, 2016.
CN Office Action for Chinese Application No. 201380014845.X dated Jul. 8, 2016.

(56) References Cited

OTHER PUBLICATIONS

CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.
CN Office Action for Chinese Application No. 20118004918.5 dated Jun. 15, 2015.
CN Office Action for Chinese Application No. 201180049184.5 dated Jul. 30, 2014.
CN Office Action for Chinese Application No. 201180049184.5 dated Mar. 4, 2016.
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 dated Oct. 27, 2015.
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).
Edwards, "Large Sheets of Graphene Film Produced for Transparent Electrodes (w/ Video)", (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Georgakilas et al., "Functionalization of Graphene: Covalent and Non-Covalent Approaches, Derivatives and Applications," Chem. Rev., (2012) 112(11), pp. 6156-6214.
Gnudi "Molecular mechanisms of proteinuria in diabetes," Biochem. Soc. Trans. 36(5): 946-949 (Oct. 2008).
Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).

Harvey "Carbon as conductor: a pragmatic view." Proceedings of the 61st IWCS Conference, http://www.iwcs.org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of Fe3 O4 nanoparticles to graphene oxide by covalent bonding." Carbon 48.11 (2010): 3139-3144.
Hone et al. "Graphene has record-breaking strength" Physicsworld.com, Jul. 17, 2008.
Huang et al., "Gene expression profile in circulating mononuclear cells afterexposure to ultrafine carbon particles," Inhalation Toxicol. 22(10): 835-846 (Aug. 2010).
Humplik, et al. "Nanostructured materials for water desalination." Nanotechnology 22.29 (2011): 292001.
International Search Report and Written Opinion dated Jan. 5, 2012 for related International Application No. PCT/US11/47800.
International Search Report and Written Opinion dated Jul. 5, 2017 from related PCT application PCT/US2017/024147.
International Search Report and Written Opinion dated Mar. 12, 2014 for International Application No. PCT/US2013/074942.
International Search Report and Written Opinion for International Application No. PCT/US2011/047800 dated Jan. 5, 2012.
International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.
International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2014/041766, dated Sep. 30, 2014.
International Search Report and Written Opinion dated Jun. 5, 2014 in International Application No. PCT/US2014/021677.
International Search Report and Written Opinion dated Jun. 6, 2014 in International Application No. PCT/US2014/023043.
International Search Report and Written Opinion dated Dec. 16, 2014, for International Application No. PCT/US2014/051011.
International Search Report and Written Opinion dated Jun. 19, 2015, in International Application No. PCT/US2015/020287.
Inui et al. "Molecular dynamics simulations of nanopore processing in a graphene sheet by using gas cluster ion beam." Applied Physics A: Materials Science & Processing 98.4 (2010): 787-794.
Israelachvili, "Intermolecular and Surface Forces," 3rd ed., Chap. 7.1, Sizes of Atoms, Molecules, and Ions, 2011, 1 page.
Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).
JP Office Action in Japanese Application No. 2015-501729 dated Dec. 9, 2016 (English translation).
JP Office Action in Japanese Application No. 2015-501729 dated Jun. 20, 2017 (English translation).
JP Office Action in Japanese Application No. 2015-501867 dated Oct. 11, 2016 (English translation).
JP Office Action in Japanese Application No. 2015-503405 dated Nov. 14, 2016 (English translation).
JP Office Action in Japanese Application No. 2015-503406 dated Dec. 6, 2016(English translation).
Kang et al., "Effect of eplerenone, enalapril and their combination treatment on diabetic nephropathy in type II diabetic rats," Nephrol. Dialysis Transplant. 24(1): 73-84 (Jan. 2009).
Kang et al., "Efficient Transfer of Large-Area Graphene Films onto Rigid Substrates by Hot Pressing," American Chemical Society Nano, 6(6): 5360-5365(May 28, 2012).
Kar et al., "Effect of glycation of hemoglobin on its interaction with trifluoperazine," Protein J. 25(3): 202-211 (Apr. 2006) (available online Jun. 6, 2006).
Kawamoto et al., "Serum high molecular weight adiponectin is associated with mild renal dysfunction in Japanese adults," J. Atherosclerosis Thrombosis 17(11): 1141-1148 (Nov. 27, 2011).

(56) References Cited

OTHER PUBLICATIONS

Khun et al. "From Microporous Regular Frameworks to Mesoporous Materials with Ultrahigh Surface Area: Dynamic reorganization of Porous Polymer Networks" JACS, 2008; vol. 130; pp. 13333-13337.
Krupka et al., "Measurements of the Sheet Resistance and Conductivity of Thin Epitaxial Graphene and SiC Films" Applied Physics Letters 96, 082101-I; Feb. 23, 2010.
Kumar et al., "Modulation of alpha-crystallin chaperone activity in diabetic rat lens by curcumin," Molecular Vision 11: 561-568 (Jul. 26, 2005).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Lucchese et al. "Quantifying ion-induced defects and Raman relaxation length in graphene." Carbon 48.5 (2010): 1592-1597.
MacLeod et al. "Supramolecular Orderinng in Oligothiophene-Fullerene Monolayers" JACS, 2009, vol. 131, pp. 16844-16850.
Mattevi et al. "A review of chemical vapour deposition of graphene on copper." Journal of Materials Chemistry 21.10 (2011): 3324-3334.
Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Nafea, et al. "Immunoisolating semi-permeable membranes for cell encapsulation: focus on hydrogels." J Control Release. 154(2): 110-122 (Sep. 5, 2011).
Nezlin, "Circulating non-immune IgG complexes in health and disease," Immunol. Lett. 122(2); 141-144 (Feb. 21, 2009) (available online Feb. 2, 2009).
Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).
Ogawa et al., "Exosome-like vesicles in Gloydius blomhoffii blomhoffii venom," Toxicon 51(6): 984-993 (May 2008) (available online Feb. 19, 2008).
Ohgawara et al. "Assessment of pore size of semipermeable membrane for immunoisolation on xenoimplatntation of pancreatic B cells using a diffusion chamber." Transplant Proc. (6): 3319-3320. 1995.
Oki et al., "Combined acromegaly and subclinical Cushing disease related to high-molecular-weight adrenocorticotropic hormone," J. Neurosurg. 110(2): 369-73 (Feb. 2009).
Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).
Osorio et al., "Effect of phlorizin on SGLT2 expression in the kidney of diabetic rats," J. Nephrol. 23(5): 541-546 (Sep.-Oct. 2010).
Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).
Pall Corporation, "Pall Water Processing Disc-Tube Filter Technology", Retrieved on Feb. 10, 2015, Retrieved from http://www.pall.com /pdfs/Fuels-and-Chemicals/Disc-Tube_Filter_Technoloqy-DT100b.pdF (15 Pages).
Plant et al. "Size-dependent propagation of Au nanoclusters through few-layer grapheme," The Royal Society of Chemistry 2013, Nanoscale.

Pollard, "Growing Graphene via Chemical Vapor" Department of Physics, Pomona College; May 2, 2011.
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1-Expressing Pancreatic Progenitor Cells Accelerates the Maturation of Insulin-Secreting Cells In Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).
Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.
SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Sethna et al., "Serum adiponectin levels and ambulatory blood pressure monitoring in pediatric renal transplant recipients," Transplantation 88(8): 1030-1037 (Oct. 27, 2009).
Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).
Swett et al, "Imagining and Sculpting Graphene on the atomic scale" Oak Ridge National Laboratory's (ORNL) Center for Nanophase Materials Sciences (CNMS) Biannual Review. 1 page.
Swett et al, "Supersonic Nanoparticle Interaction with Suspended CVD Graphene", Microsc. Microanal. 22 (Suppl 3): 1670-1671 (Jul. 25, 2016).
Takata et al., "Hyperresistinemia is associated with coexistence of hypertension and type 2 diabetes," Hypertension 51. 2 (Feb. 2008): 534-9.
Tamborlane et al., "Continuous Glucose Monitoring and Intensive Treatment of Type 1 Diabetes" N Engl J Med 359;14: 1464-1476 (Oct. 2, 2008).
Tanugi et al., "Nanoporous Graphene Could Outperform Best Commercial Water Desalination Techniques," ; ACS 2012; Jun. 25, 2012; Weftec 2012; Sep. 29-Oct. 3.
Totani et al. "Gluten binds cytotoxic compounds generated in heated frying oil." Journal of oleo science 57.12 (2008): 683-690.
Tsukamoto et al. "Purification, characterization and biological activities of a garlic oliqosaccharide," Journal of UOEH 30.2 (Jun. 1, 2008): 147-57.
TW Office Action in Taiwanese Application No. 102146079 dated Apr. 14, 2017. 9 Pages.(English translation).
TW Search Report in Taiwanese Application No. 102146079 dated Apr. 14, 2017. 1 page.
UMEA Universitet "Graphene nanoscrolls are formed by decoration of magnetic nanoparticles." ScienceDaily. Aug. 15, 2013. https://www.sciencedaily.com/releases/2013/08/130815084402.htm (3 pages).
U.S. Notice of Allowance for U.S. Appl. No. 12/868,150 dated Sep. 25, 2012.
U.S. Notice of Allowance for U.S. Appl. No. 13/548,539 dated Aug. 18, 2015.

(56) References Cited

OTHER PUBLICATIONS

U.S. Notice of Allowance for U.S. Appl. No. 13/548,539 dated Jul. 23, 2015.
U.S. Notice of Allowance for U.S. Appl. No. 13/719,579 dated May 20, 2016.
U.S. Notice of Allowance for U.S. Appl. No. 13/795,276 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 13/923,503 dated Oct. 14, 2016.
U.S. Notice of Allowance for U.S. Appl. No. 13/923,503 dated Oct. 5, 2016.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/610,770 dated May 5, 2017.
U.S. Notice of Allowance in U.S. Appl. No. 14/656,580 dated May 8, 2017.
U.S. Notice of Allowance in U.S. Appl. No. 14/819,273 dated Jun. 9, 2017.
U.S. Notice of Allowance in U.S. Appl. No. 15/099,464 dated Jun. 16, 2017.
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.
U.S. Office Action for U.S. Appl. No. 13/923,503 dated Mar. 22, 2016.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016.
U.S. Office Action for U.S. Appl. No. 14/203,655 dated Aug. 10, 2016.
U.S. Office Action for U.S. Appl. No. 14/656,190 dated May 18, 2017.
U.S. Office Action for U.S. Appl. No. 14/656,657 dated Jul. 7, 2017.
U.S. Office Action for U.S. Appl. No. 14/686,452 dated Jun. 9, 2017.
U.S. Office Action for U.S. Appl. No. 14/843,944 dated Jun. 23, 2017.
U.S. Office Action for U.S. Appl. No. 14/856,471 dated May 31, 2017.
U.S. Office Action for U.S. Appl. No. 14/858,741 dated Dec. 1, 2016.
U.S. Office Action for U.S. Appl. No. 15/289,944 dated Feb. 9, 2017.
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/193,007 dated Apr. 24, 2017.
U.S. Office Action in U.S. Appl. No. 14/656,617 dated Apr. 4, 2017.
U.S. Office Action on U.S. Appl. No. 14/656,335 dated Apr. 25, 2017.
U.S. Office Action on U.S. Appl. No. 15/332,982 dated Jan. 30, 2017.
U.S. Supplemental Notice of Allowance for U.S. Appl. No. 13/795,276 dated Nov. 29, 2016.
Vallon,"Micropuncturing the nephron," Pflugers Archiv : European journal of physiology 458. 1 (May 2009): 189-201.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de CI's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vriens et al. "Methodological considerations in quantification of oncological FDG PET studies." European journal of nuclear medicine and molecular imaging 37.7 (2010): 1408-1425.
Wang et al., "Direct Observation of a Long-Lived Single-Atom Catalyst Chiseling Atomic Structures in Graphene," Nano Lett., 2014, pp. A-F.
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wang et al.,"What is the role of the second "structural" NADP+-binding site in human glucose 6-phosphate dehydrogenase?," Protein science a publication of the Protein Society 17. 8 (Aug. 2008): 1403-11.
Wei et al., "Synthesis of N-doped graphene by chemical vapor deposition and its electrical properties", Nano Lett. 2009 9 1752-58.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie et al., "Fractionation and characterization of biologically-active polysaccharides from Artemisia tripartite," Phytochemistry 69. 6 (Apr. 2008): 1359-71.
Xie, et al. "Controlled fabrication of high-quality carbon nanoscrolls from monolayer graphene." Nano letters 9.7 (2009): 2565-2570.
Yagil et al. "Nonproteinuric diabetes-associated nephropathy in the Cohen rat model of type 2 diabetes" Diabetes 54. 5 (May 2005): 1487-96.
Zan et al. "Interaction of Metals with Suspended Graphene Observed by Transmission Electron Microscopy", J. Phys. Chem. Lett., Mar. 8, 2012, 3, 953-958.

(56) References Cited

OTHER PUBLICATIONS

Zhang et al. "Effect of Chemical Oxidation on the Structure of Single-Walled Carbon Nanotubes", J. Phys. Chem., Feb. 12, 2003, B 107 3712-8.
Zhang et al. "Method for anisotropic etching of graphite or graphene" Institute of Physics, Chinese Academy of Sciences; PEOP. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al. "Isolation and activity of an alpha-amylase inhibitor from white kidney beans," Yao xue xue bao =Acta pharmaceutica Sinica 42. 12 (Dec. 2007): 1282-7.
Zhao, et al. "Efficient preparation of large-area graphene oxide sheets for transparent conductive films." ACS nano 4.9 (2010): 5245-5252.
Zhou, K., et al., "One-pot preparation of graphene/ Fe3O4 composites by a solvothermal reaction," New J. Chem., 2010, 34, 2950.
Zhu et al. "Carbon Nanotubes in Biomedicine and Biosensing", Carbon Nanotubes-Growth and Applications, InTech, (Aug. 9, 2011) Chapter 6: pp. 135-162. Available from: https://www.intechopen.com/books/carbon-nanotubes-growth-and-applications/carbon-nanotubes-in-biomedicine-and-biosensing.
Ziegelmeier et al. "Adipokines influencing metabolic and cardiovascular disease are differentially regulated in maintenance hemodialysis," Metabolism: clinical and experimental 57. 10 (Oct. 2008): 1414-21.
Zirk et al. "A refractometry-based glucose analysis of body fluids," Medical engineering & physics 29. 4 (May 2007): 449-58.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages).
U.S. Notice of Allowance in U.S. Appl. No. 14/610,770 dated Jan. 23, 2017.
U.S. Notice of Allowance in U.S. Appl. No. 14/856,198 dated Feb. 10, 2017.
U.S. Notice of Allowance in U.S. Appl. No. 14/856,198 dated Mar. 1, 2017.
U.S. Office Action in U.S. Appl. No. 14/609,325 dated Feb. 16, 2017.
U.S. Office Action in U.S. Appl. No. 14/193,007 dated Mar. 23, 2017.
U.S. Office Action in U.S. Appl. No. 14/656,580 dated Feb. 9, 2017.
U.S. Office Action in U.S. Appl. No. 15/099,464 dated Mar. 10, 2017.
European Extended Search Report in Application No. 15837617.8 dated Mar. 22, 2018 (9 pages).
Singapore Written Opinion for Appl. Ser. No. 11201607584P dated Jun. 8, 2018 (7 pages).
U.S. Non-Final Office Action for U.S. Appl. No. 15/099,410 dated Jun. 13, 2018 (15 pages).
U.S. Notice of Allowance for U.S. Appl. No. 15/453,441 dated Jun. 12, 2018 (8 pages).
U.S. Office Action for U.S. Appl. No. 15/099,056 dated May 29, 2018 (33 pages).
U.S. Office Action for U.S. Appl. No. 15/099,289 dated Jun. 7, 2018 (16 pages).
Australian Office Action in Application No. 2013235234 dated Dec. 19, 2017 (5 pages).
Japanese Office Action in Application No. 2017-002652 dated Nov. 24, 2017 (with English translation) (7 pages).
Chu, L., et al., "Porous graphene sandwich/poly(vinylidene fluoride) composites with high dielectric properties," Composites Science and Technology, 86, (2013), pp. 70-75.
European Extended Search Report in Application No. 15743307.9 dated Nov. 15, 2017 (14 pages).
European Extended Search Report in Application No. 15755350.4 dated Oct. 30, 2017 (9 pages).
European Extended Search Report in Application No. 15762019.6 dated Nov. 20, 2017 (12 pages).
European Extended Search Report in Application No. 15762213.5 dated Oct. 10, 2017 (8 pages).
Gu et al., "One-step synthesis of porous graphene-based hydrogels containing oil droplets for drug delivery", Royal Society of Chemistry (RSC), vol. 4, No. 7, Jan. 1, 2014, pp. 3211-3218.
Japanese Office Action in Application No. 2015-549508 dated Nov. 7, 2017 (with English translation) (2 pages).
Kim et al., "Selective Gas Transport Through Few-Layered Graphene and Graphene Oxide Membranes", Science, vol. 342, Oct. 4, 2013, pp. 91-95 (6 total pages).
Singapore Search Report and Written Opinion in Application No. 11201609272T dated Oct. 5, 2017 (11 pages).
U.S. Notice of Allowance in U.S. Appl. No. 15/099,464 dated Nov. 16, 2017 (5 pages).
U.S. Notice of Allowance in U.S. Appl. No. 15/332,982 dated Nov. 1, 2017 (9 pages).
U.S. Office Action in U.S. Appl. No. 14/707,808 dated Nov. 6, 2017 (27 pages).
U.S. Office Action in U.S. Appl. No. 15/099,193 dated Dec. 28, 2017 (25 pages).
U.S. Office Action in U.S. Appl. No. 15/099,304 dated Nov. 24, 2017 (23 pages).
Wang, M., et al., "Interleaved Porous Laminate Composed of Reduced Graphene Oxide Sheets and Carbon Black Spacers by In-Situ Electrophoretic Deposition," The Royal Society of Chemistry (2014), pp. 1-3.
Wimalasiri, Y., et al., "Carbon nanotube/graphene composite for enhanced capacitive deionization performance," Carbon 59 (2013), pp. 464-471.
Chen et al., "Hierarchically porous graphene-based hybrid electrodes with excellent electrochemical performance", Journal of Materials Chemistry A: Materials for Energy and Sustainability, vol. 1, No. 33, Jan. 1, 2013, pp. 9409-9413.
Chinese Office Action in Application No. 201580006829.5 dated Jan. 23, 2018 (with English translation) (13 pages).
European Extended Search Report in Application No. 15786691.4 dated Dec. 1, 2017 (10 pages).
European Extended Search Report in Application No. 15789852.9 dated Dec. 6, 2017 (8 pages).
Japanese Office Action in Application No. 2017-042023 dated Jan. 9, 2018 (with English translation) (9 pages).
Singapore Search Report and Written Opinion in Application No. 11201701654U dated Dec. 6, 2017 (6 pages).
Taiwanese Office Action in Application No. 102146079 dated Dec. 12, 2017 (with English translation) (4 pages).
U.S. Notice of Allowance in U.S. Appl. No. 14/843,944 dated Feb. 9, 2018 (9 pages).
U.S. Office Action for U.S. Appl. No. 15/099,482 dated Feb. 23, 2018 (9 pages).
U.S. Office Action in U.S. Appl. No. 14/609,325 dated Jan. 16, 2018 (11 pages).
U.S. Office Action in U.S. Appl. No. 14/656,190 dated Jan. 10, 2018 (14 pages).
U.S. Office Action in U.S. Appl. No. 14/856,471 dated Jan. 11, 2018 (36 pages).
U.S. Office Action in U.S. Appl. No. 15/099,099 dated Feb. 15, 2018 (13 pages).
U.S. Office Action in U.S. Appl. No. 15/099,588 dated Feb. 1, 2018 (6 pages).
Wang et al., "Preparation of high-surface-area carbon nanoparticle/ graphene composites", Carbon, Elsevier, Oxford, GB, vol. 50, No. 10, Apr. 8, 2012, pp. 3845-3853.
Adiga et al., "Nanoporous Materials for Biomedical Devices," JOM 60: 26-32 (Mar. 25, 2008).
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
Apel, "Track etching technique in membrane technology," Radiation Measurements 34(1-6): 559-566 (Jun. 2001).

(56) References Cited

OTHER PUBLICATIONS

Bae et al., "Roll-to-roll production of 30-inch graphene films for transparent electrodes," Nature Nanotechnology 5: 574-578 (Jun. 20, 2010).
Bai et al., "Graphene nanomesh," Nature Nanotechnology 5: 190-194 (Feb. 14, 2010).
Baker. (2004). "Track-etch Membranes." In Membrane Technology and Applications (2nd ed., pp. 92-94). West Sussex, England: John Wiley & Sons.
Butler et al. "Progress, Challenges, and Opportunities in Two-Dimensional Materials Beyond Graphene", Materials Review 7(4): 2898-2926 (Mar. 6, 2013).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13 (Feb. 10, 2011).
Clochard. (undated). "Radiografted track-etched polymer membranes for research and application." [Scholarly project]. In Laboratoire Des Solides Irradies. Retrieved Jun. 2, 2016, from http://iramis.cea.fr/radiolyse/5juin2015/Clochard.pdf.
Cohen-Tanugi et al, "Water Desalination across Nanoporous Graphene," ACS Nano Letters 12(7): 3602-3608 (Jun. 5, 2012).
Cohen-Tanugi, "Nanoporous graphene as a water desalination membrane," Thesis: Ph.D., Massachusetts Institute of Technology, Department of Materials Science and Engineering (Jun. 2015).
Colton, "Implantable biohybrid artificial organs," Cell Transplantation 4(4): 415-436 (Jul.-Aug. 1995).
Desai et al., "Nanoporous microsystems for islet cell replacement," Advanced Drug Delivery Reviews 56: 1661-1673 (Jul. 23, 2004).
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 58-63 (Jan. 5, 2009).
Gimi et al., "A Nanoporous, Transparent Microcontainer for Encapsulated Islet Therapy," J. Diabetes Sci. Tech. 3(2): 1-7 (Mar. 2009).
Jiang et al., "Porous Graphene as the Ultimate Membrane for Gas Separation," Nano Letters 9(12): 4019-4024 (Sep. 23, 2009).
Joshi et al., "Precise and ultrafast molecular sieving through graphene oxide membranes", Science 343(6172): 752-754 (Feb. 14, 2014).
Kanani et al., "Permeability—Selectivity Analysis for Ultrafiltration: Effect of Pore Geometry," NIH-PA Author Manuscript, PMC, (Mar. 1, 2011), also published in J. Memb. Sci. 349(1-2): 405 (Mar. 1, 2010).
Karan et al., "Ultrafast Viscous Permeation of Organic Solvents Through Diamond-Like Carbon Nanosheets," Science 335: 444-447 (Jan. 27, 2012).
Kim et al., "Fabrication and Characterization of Large Area, Semiconducting Nanoperforated Graphene Materials," Nano Letters 10(4): 1125-1131 (Mar. 1, 2010).
Kim et al., "The structural and electrical evolution of graphene by oxygen plasma-induced disorder," Nanotechnology IOP 20(375703): 1-8 (Aug. 26, 2009).
Koski and Cui, "The New Skinny in Two-Dimensional Nanomaterials", ACS Nano 7(5): 3739-3743 (May 16, 2013).
Liu et al., "Atomically Thin Molybdenum Disulfide Nanopores with High Sensitivity for DNA Translocation," ACS Nano 8(3): 2504-2511 (Feb. 18, 2014).
Liu et al., "Graphene Oxidation: Thickness-Dependent Etching and Strong Chemical Doping," Nano Letters 8(7): 1965-1970 (Jun. 19, 2008).
Mishra et al., "Functionalized Graphene Sheets for Arsenic Removal and Desalination of Sea Water," Desalination 282: 39-45 (Nov. 1, 2011).
Morse, "Scalable Synthesis of Semiconducting Nanopatterned Graphene Materials," InterNano Resources for Nanomanufacturing (undated). Retrieved Jun. 2, 2016 from: http://www.internano.org/node/345.
Nair et al., "Unimpeded Permeation of Water Through Helium-Leak-tight Graphene-Based Membranes," Science 335: 442-444 (Jan. 27, 2012).
O'Hern et al. "Selective Molecular Transport through Intrinsic Defects in a Single Layer of CVD Graphene," ACS Nano, 6(11): 10130-10138 (Oct. 2, 2012).
O'Hern et al., "Selective Ionic Transport through Tunable Subnanometer Pores in Single-Layer Graphene Membranes," Nano Letters 14(3): 1234-1241 (Feb. 3, 2014).
Paul, "Creating New Types of Carbon-Based Membranes," Science 335: 413-414 (Jan. 27, 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sint et al., "Selective Ion Passage through Functionalized Graphene Nanopores," JACS 130: 16448-16449 (Nov. 14, 2008).
Suk et al., "Water Transport Through Ultrathin Graphene," Journal of Physical Chemistry Letters 1(10): 1590-1594 (Apr. 30, 2010).
Tan et al., "Beta-cell regeneration and differentiation: how close are we to the 'holy grail'?" J. Mol. Encodrinol. 53(3): R119-R129 (Dec. 1, 2014).
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East (Jul. 2, 2012). Retrieved Jun. 1, 2016 from: natureasia.com/en/nmiddleeast/article/10.1038/nmiddleeast.2012.92?WT.mc_id=FBK_NatureMEast].
Wikipedia, "Ion track." Jun. 1, 2016. Retrieved Jun. 1, 2016 from: en.wikipedia.org/wiki/ion_track.
Xu et al., "Graphene-like Two-Dimensional Materials", Chemical Reviews 113: 3766-3798 (Jan. 3, 2013).
Zan et al., "Graphene Reknits Its Holes," Nano Lett. 12(8): 3936-3940 (Jul. 5, 2012).
Zhao et al. "Two-Dimensional Material Membranes: An Emerging Platform for Controllable Mass Transport Applications," Small 10(22): 4521-4542 (Sep. 10, 2014).
EPO Extended Search Report for European Application No. 171684883.5 dated Jul. 25, 2017 (8 pages).
EPO Supplementary Search Report for European Application No. 15762019.6 dated Aug. 9, 2017 (16 pages).
U.S. Notice of Allowance in U.S. Appl. No. 14/610,770 dated Sep. 26, 2017. (12 pages).
U.S. Notice of Allowance in U.S. Appl. No. 15/332,982 dated Sep. 21, 2017. (5 pages).
U.S. Office Action in U.S. Appl. No. 15/099,099 dated Oct. 5, 2017 (11 pages).
U.S. Office Action in U.S. Appl. No. 15/099,447 dated Oct. 3, 2017 (21 pages).
Weisen, et al., "Fabrication of nanopores in a graphene sheet with heavy ions: A molecular dynamics study", Journal of Applied Physics 114, 234304 (2013), pp. 234304-1 to 234304-6.
Allen et al., "Craters on silicon surfaces created by gas cluster ion impacts," Journal of Applied Physics, 92(7): 3671-3678 (Oct. 2002).
Atmeh et al., "Albumin Aggregates: Hydrodynamic Shape and Physico-Chemical Properties," Jordan Journal of Chemistry, 2(2): 169-182 (2007).
Chen et al., "Mechanically Strong, Electrically Conductive, and Biocompatible Graphene Paper," Adv. Mater., 20(18): 3557-3561 (Sep. 2008) (available online Jul. 2008).
CN Office Action in Chinese Application No. 201380013988.9 dated Aug. 18, 2016 (English translation not readily available).
Fuertes, "Carbon composite membranes from Matrimid® and Kapton® polyimides for gas separation," Microporous and Mesoporous Materials, 33: 115-125 (1991).
Galashev, "Computer study of the removal of Cu from the graphene surface using Ar clusters," Computational Materials Science, 98: 123-128 (Feb. 2015) (available online Nov. 2014).
International Search Report and Written Opinion in PCT/US2015/013599 dated Jul. 20, 2015.

(56) References Cited

OTHER PUBLICATIONS

International Search Report and Written Opinion in PCT/US2015/013805 dated Apr. 30, 2015.
International Search Report and Written Opinion in PCT/US2015/018114 dated Jun. 3, 2015.
International Search Report and Written Opinion in PCT/US2015/020246 dated Jun. 10, 2015.
International Search Report and Written Opinion in PCT/US2015/020296 dated Jun. 17, 2015.
International Search Report and Written Opinion in PCT/US2015/028948 dated Jul. 16, 2015.
International Search Report and Written Opinion in PCT/US2015/029932 dated Oct. 6, 2015.
Inui et al., "Molecular dynamics simulations of nanopore processing in a graphene sheet by using gas cluster ion beam," Appl. Phys. A, 98: 787-794 (Mar. 2010) (available online Dec. 2009).
Koh et al., "Sensitive NMR Sensors Detect Antibodies to Influenza," NIH PA Author Manuscript PMC (Apr. 2009), also published in Angew. Chem. Int'l Engl, 47(22): 4119-4121 (May 2008) (available online Apr. 2008).
Lehtinen et al., "Cutting and controlled modification of graphene with ion beams," Nanotechnology, 22: 175306 (8 pages) (Mar. 2011).
Matteucci et al., "Transport of gases and Vapors in Glass and Rubbery Polymers," in Materials Science of Membranes for Gas and Vapor Separation. (Yampolskii et al., eds. 2006) (available online Jun. 2006).
O'Hern et al., "Development of process to transfer large areas of LPCVD graphene from copper foil to a porous support substrate," 1-62 (M.S. Thesis, Massachusetts Institute of Technology, Thesis) (Sep. 2011).
Plant et al. "Size-dependent propagation of Au nanoclusters through few-layer graphene," Nanoscale, 6: 1258-1263 (2014) (available online Oct. 2013).
Popok. "Cluster Ion Implantation in Graphite and Diamond: Radiation Damage and Stopping of Cluster Constituents," Reviews on Advanced Materials Science, 38(1): 7-16 (2014).
Russo et al., "Atom-by-atom nucleation and growth of graphene nanopores," PNAS 109(16): 5953-5957 (Apr. 2012).
U.S. Notice of Allowance in U.S. Appl. No. 14/610,770 dated Aug. 12, 2016.
U.S. Office Action in U.S. Appl. No. 14/656,190 dated Aug. 29, 2016.
U.S. Office Action for U.S. Appl. No. 14/656,580 dated Jun. 2, 2016.
U.S. Office Action in U.S. Appl. No. 14/819,273 dated Jul. 6, 2016.
U.S. Office Action for U.S. Appl. No. 14/856,198 dated Jun. 3, 2016.
Yoon, "Simulations show how to turn graphene's defects into assets," Sciencedaily (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: (Jan. 2015) (available online Nov. 2014).
Zhang et al. Modern Thin-Film Technology 284-285 (Metallurgical Industry Press, 1st ed. 2009) (English translation not readily available).
Zhao et al. (2012), "Effect of SiO2 substrate on the irradiation-assisted manipulation of supported graphene: a molecular dynamics study," Nanotechnology 23(28): 285703 (Jul. 2012) (available online Jun. 2012).
Zhao et al. (May 2012), "Drilling Nanopores in Graphene with Clusters: A Molecular Dynamics Study," J. Phys. Chem. C, 116(21): 11776-11178 (2012) (available online May 2012).
Notice of Allowance for U.S. Appl. No. 14/819,273 dated Oct. 28, 2016.
U.S. Office Action for U.S. Appl. No. 14/193,007 dated Oct. 21, 2016.
U.S. Office Action for U.S. Appl. No. 14/193,007 dated Dec. 21, 2015.
U.S. Office Action for U.S. Appl. No. 14/193,007 dated Jul. 1, 2016.
Dong et al., "Growth of large-sized graphene thin-films by liquid precursor-based chemical vapor deposition under atmospheric pressure," Carbon 49(11): 3672-3678 (May 2011).
Hong et al., "Graphene multilayers as gates for multi-week sequential release of proteins from surfaces," NIH-PA Author Manuscript PMC (Jun. 1, 2014), also published in ACS Nano, Jan. 24, 2012; 6(1): 81-88 (first published online Dec. 29, 2011).
Hu et al., "Enabling graphene oxide nanosheets as water separation membranes," Environmental Science & Technology, 47(8): 3715-3723 (Mar. 14, 2013).
International Search Report and Written Opinion of the International Searching Authority dated Jul. 22, 2016, from related international patent application PCT/US2016/027607.
International Search Report and Written Opinion of the International Searching Authority dated Jul. 22, 2016, from related international patent application PCT/US2016/027616.
International Search Report and Written Opinion of the International Searching Authority dated Jul. 22, 2016, from related PCT application PCT/US2016/027596.
International Search Report and Written Opinion of the International Searching Authority dated Jul. 22, 2016, from related PCT application PCT/US2016/027603.
International Search Report and Written Opinion of the International Searching Authority dated Jul. 22, 2016, from related PCT application PCT/US2016/027610.
International Search Report and Written Opinion of the International Searching Authority dated Jul. 22, 2016, from related PCT application PCT/US2016/027612.
International Search Report and Written Opinion of the International Searching Authority dated Jun. 22, 2016, from related PCT application PCT/US2016/027637.
Kurapati et al., "Graphene oxide based multilayer capsules with unique permeability properties: facile encapsulation of multiple drugs," Chemical Communication 48: 6013-6015 (Apr. 25, 2012).
Li et al., "3D graphene oxide-polymer hydrogel: near-infrared light-triggered active scaffold for reversible cell capture and on-demand release," Advanced Materials 25: 6737-6743 (Oct. 7, 2013).
Marquardt et al., "Hybrid materials of platinum nanoparticles and thiol-functionalized graphene derivatives," Carbon 66: 285-294 (Jan. 2014; first published online Sep. 12, 2013).
Nam et al., "Monodispersed PtCo nanoparticles on hexadecyltrimethylammonium bromide treated graphene as an effective oxygen reduction reaction catalyst for proton exchange membrane fuel cells," Carbon 50: 3739-3747 (Aug. 2012; first published online Apr. 5, 2012).
Nandamuri et al., "Chemical vapor deposition of graphene films," Nanotechnology 21(14): 1-4 (Mar. 10, 2010).
Nayini et al., "Synthesis and characterization of functionalized carbon nanotubes with different wetting behaviors and their influence on the wetting properties of carbon nanotubes/polymethylmethacrylate coatings," Progress in Organic Coatings 77(6): 1007-1014 (Mar. 2014).
Sun et al., "Growth of graphene from solid carbon sources," Nature 468(7323): 549-552 (Nov. 25, 2010; including corrigendum in Nature 471(7336): 124 (Mar. 2011).
Tang et al., "Highly wrinkled cross-linked graphene oxide membranes for biological and charge-storage applications," Small 8(3): 423-431 (Feb. 6, 2012; first published online Dec. 13, 2011).
Clochard. (undated). Radiografted track-etched polymer membranes for research and application [Scholarly project]. In Laboratoire Des Solides Irradies. Retrieved Jun. 2, 2016, from http://iramis.cea.fr/radiolyse/5juin2015/Clochard.pdf.
International Search Report dated Dec. 4, 2015, in related international application PCT/US2015/048205.
International Search Report dated Jun. 10, 2015, from related international application PCT/US15/20201.
PCT/US2015/018114, Feb. 27, 2015.
U.S. Appl. No. 14/858,741, filed Sep. 18, 2015.
U.S. Appl. No. 14/193,007, filed Feb. 28, 2014.
U.S. Appl. No. 14/856,471, filed Sep. 16, 2015.

(56) References Cited

OTHER PUBLICATIONS

U.S. Appl. No. 15/099,295, filed Apr. 14, 2016.
U.S. Appl. No. 15/099,410, filed Apr. 14, 2016.
U.S. Appl. No. 15/099,420, filed Apr. 14, 2016.
U.S. Appl. No. 15/099,289, filed Apr. 14, 2016.
U.S. Appl. No. 15/099,447, filed Apr. 14, 2016.
U.S. Appl. No. 15/099,269, filed Apr. 14, 2016.
U.S. Appl. No. 15/099,239, filed Apr. 14, 2016.
U.S. Appl. No. 15/099,464, filed Apr. 14, 2016.
U.S. Appl. No. 15/099,276, filed Apr. 14, 2016.
U.S. Appl. No. 15/099,482, filed Apr. 14, 2016.
U.S. Appl. No. 15/099,056, filed Apr. 14, 2016.
U.S. Appl. No. 15/099,099, filed Apr. 14, 2016.
U.S. Appl. No. 15/308,351, filed Nov. 1, 2016.
U.S. Appl. No. 14/656,190, filed Mar. 12, 2015.
U.S. Appl. No. 15/099,304, filed Apr. 14, 2016.
U.S. Appl. No. 15/099,588, filed Apr. 14, 2016.
PCT/US2015/028948, May 1, 2015.
U.S. Appl. No. 14/843,944, filed Sep. 2, 2015.
U.S. Appl. No. 15/099,193, filed Apr. 14, 2016.
U.S. Appl. No. 15/336,545, filed Oct. 27, 2016.
U.S. Appl. No. 15/289,944, filed Oct. 10, 2016.
U.S. Pat. No. 9,193,587, Nov. 24, 2015, U.S. Appl. No. 13/548,539, filed Jul. 13, 2012.
U.S. Appl. No. 13/422,753, filed Mar. 16, 2012.
U.S. Pat. No. 8,361,321, Jan. 29, 2013, U.S. Appl. No. 12/868,150, filed Aug. 25, 2010.
U.S. Pat. No. 9,475,709, Oct. 25, 2016, U.S. Appl. No. 13/719,579, filed Dec. 19, 2012.
U.S. Pat. No. 9,028,663, May 12, 2015, U.S. Appl. No. 13/804,085, filed Mar. 14, 2013.
U.S. Appl. No. 14/686,452, filed Apr. 14, 2015.
U.S. Pat. No. 9,463,421, Oct. 11, 2016, U.S. Appl. No. 13/803,958, filed Mar. 14, 2013.
U.S. Pat. No. 9,095,823, Aug. 4, 2015, U.S. Appl. No. 13/802,896, filed Mar. 14, 2013.
U.S. Pat. No. 9,592,475, Mar. 14, 2017, U.S. Appl. No. 14/203,655, filed Mar. 11, 2014.
U.S. Pat. No. 9,480,952, Nov. 1, 2016, U.S. Appl. No. 14/200,195, filed Mar. 7, 2014.
U.S. Pat. No. 9,567,224, Feb. 14, 2017, U.S. Appl. No. 13/795,276, filed Mar. 12, 2013.
U.S. Appl. No. 14/031,300, filed Sep. 19, 2013.
U.S. Pat. No. 9,505,192, Nov. 29, 2016, U.S. Appl. No. 14/200,530, filed Mar. 7, 2014.
U.S. Pat. No. 9,572,918, Feb. 21, 2017, U.S. Appl. No. 13/923,503, filed Jun. 21, 2013.
U.S. Appl. No. 13/779,963, filed Feb. 28, 2013.
U.S. Appl. No. 14/656,580, filed Mar. 12, 2015.
U.S. Pat. No. 9,610,546, Apr. 4, 2017, U.S. Appl. No. 14/856,198, filed Sep. 16, 2015.
U.S. Appl. No. 14/656,335, filed Mar. 12, 2015.
U.S. Appl. No. 14/656,657, filed Mar. 12, 2015.
U.S. Appl. No. 14/656,617, filed Mar. 12, 2015.
U.S. Appl. No. 13/480,569, filed May 25, 2012.
U.S. Appl. No. 14/754,531, filed Jun. 29, 2015.
U.S. Appl. No. 14/610,770, filed Jan. 30, 2015.
U.S. Appl. No. 14/609,325, filed Jan. 29, 2015.
U.S. Appl. No. 14/819,273, filed Aug. 5, 2015.
U.S. Pat. No. 9,242,865, Jan. 26, 2016, U.S. Appl. No. 14/192,796, filed Feb. 27, 2014.
U.S. Appl. No. 14/707,808, filed May 8, 2015.
U.S. Appl. No. 15/589,135, filed May 8, 2017.
U.S. Appl. No. 15/332,982, filed Oct. 24, 2016.
U.S. Appl. No. 15/410,457, filed Jan. 19, 2017.
U.S. Appl. No. 15/453,441, filed Mar. 8, 2017.
U.S. Appl. No. 14/971,922, filed Dec. 16, 2015.
U.S. Pat. No. 9,169,575, Oct. 27, 2015, U.S. Appl. No. 14/195,802, filed Mar. 3, 2014.
Office Action for Indian Ser. No. 1566/DELNP/2013 dated Feb. 2, 2018 (7 pages).
Office Action for Japanese Appl. Ser. No. 2016-521448 dated Mar. 16, 2018 (5 pages).
Skrzypek et al., "Pancreatic islet macroencapsulation using microwell porous membranes", Scientific Reports, 7: 9186 | DOI:10.1038/s41598-017-09647-7, Aug. 23, 2017 (12 pages).
U.S. Notice of Allowance for U.S. Appl. No. 15/099,464 dated Feb. 28, 2018 (5 pages).
U.S. Office Action for U.S. Appl. No. 15/099,276 dated Mar. 22, 2018 (13 pages).
U.S. Office Action for U.S. Appl. No. 15/453,441 dated Mar. 22, 2018 (7 pages).
Bose et al.,"Microfabricated immune-isolating devices for transplanting therapeutic cells in vivo", Koch Institute of Integrative Cancer Research, Massachusetts Institute of Technology, Undated (1 page).
Indian Office Action for Appl. Ser. No. 7731/DELNP/2014 dated Jul. 26, 2018 (6 pages).
Japanese Office Action for Appl. Ser. No. 2017-002652 dated Jul. 3, 2018 (8 pages).
Linnert, "Welding Metallurgy—Carbon and Alloy Steels", vol. I—Fundamentals (4th Edition), Chapter 2—The Structure of Metals, GML Publications, American Welding Society (AWS), Year: 1994, pp. 17-74. Retrieved from app.knovel.com/hotlink/pdf/id:kt0095RCL3/welding-metallurgy-carbon/structure-metals.
U.S. Final Office Action for U.S. Appl. No. 14/707,808 dated Jun. 27, 2018 (28 pages).
U.S. Final Office Action for U.S. Appl. No. 15/099,482 dated Aug. 27, 2018 (10 pages).
U.S. Non-Final Office Action for U.S. Appl. No. 15/099,239 dated Jul. 12, 2018 (31 pages).
U.S. Non-Final Office Action for U.S. Appl. No. 15/099,304 dated Aug. 27, 2018 (22 pages).
Vatanpour et al., "Fabrication and characterization of novel antifouling nanofiltration membrane prepared from oxidized multiwalled carbon nanotube/polyethersulfone nanocomposite", Journal of Membrane Science, vol. 375, Elsevier, Apr. 6, 2011, pp. 284-294.
Zhang et al., "Synergetic effects of oxidized carbon nanotubes and graphene oxide on fouling control and anti-fouling mechanism of polyvinylidene fluoride ultrafiltration membranes", Journal of Membrane Science, vol. 448, Elsevier, Aug. 7, 2013, pp. 81-92.

TWO-DIMENSIONAL MEMBRANE STRUCTURES HAVING FLOW PASSAGES

BACKGROUND

Two-dimensional membranes are materials with a thickness on an atomic scale. Potential applications of two-dimensional membranes are widespread, including their use in filtration, barrier, and separation devices. Due to their atomic-level thickness, however, two-dimensional membranes often need to be disposed onto a support substrate to provide the needed mechanical support for its intended use. In addition, the support substrate may provide enhanced biocompability and/or easier device integration to the membrane structure.

When a two-dimensional membrane is applied to a support substrate, a large fraction of the pores present in the two-dimensional membrane do not overlap with the passages present in the support substrate. Thus, fluid may only flow through those pores that overlap with the support substrate passages. Those pores that do not overlap with the support substrate passages are not utilized, resulting in low overall pore utilization in the membrane. In many cases, the overall pore utilization for these structures can be as low as 5%, leading to a lower overall fluid flow through the two-dimensional membrane structure.

To increase flow through the two-dimensional membrane structure and to increase overall pore utilization, one method may be to increase the density of pores in the two-dimensional membrane such that the amount of pores that overlap with the support substrate channels is increased. However, increasing the density of pores in the membrane may add to the mechanical strain on the two-dimensional membrane and may make transferability of large-scale membranes (e.g., >1 cm$^2$) to the support substrate difficult.

SUMMARY

In some embodiments, a two-dimensional membrane layered structure may include a support substrate layer having a plurality of substrate passages configured to allow fluid to flow therethrough, a two-dimensional membrane layer disposed on an upper surface of the support substrate layer, and a plurality of flow passages disposed between the support substrate layer and the two-dimensional membrane layer. The two-dimensional membrane layer may have a plurality of pores configured to allow fluid to flow therethrough. The plurality of pores may comprise a first portion of pores that overlap with the plurality of substrate passages and a second portion of pores that do not overlap with the plurality of substrate passages. The plurality of flow passages may be configured to allow fluid to flow through the second portion of pores to the plurality of substrate passages.

In some embodiments, the two-dimensional membrane layered structure may comprise a plurality of interlayer supports disposed on an upper surface of the support substrate layer. The plurality of interlayer supports may form the plurality of flow passages.

In some embodiments, the two-dimensional membrane layered structure may comprise a plurality of grooves formed on an upper surface of the support substrate layer. The plurality of grooves may form the plurality of flow passages.

In some embodiments, the two-dimensional membrane layered structure may comprise a plurality of interlayer supports disposed on an upper surface of the support substrate layer and a plurality of grooves formed on an upper surface of the support substrate layer. The plurality of interlayer supports and the plurality of grooves may form the plurality of flow passages.

In some embodiments, a two-dimensional membrane layered structure may include a support substrate layer having a plurality of substrate passages configured to allow fluid to flow therethrough, a two-dimensional membrane layer disposed on an upper surface of the support substrate layer, and a plurality of interlayer supports disposed on the upper surface of the support substrate layer. The two-dimensional membrane layer may have a plurality of pores configured to allow fluid to flow therethrough. The plurality of pores may comprise a first portion of pores that overlap with the plurality of substrate passages and a second portion of pores that do not overlap with the plurality of substrate passages. The plurality of interlayer supports may be configured to form a plurality of flow passages that allow fluid to flow through the second portion of pores to the plurality of substrate passages.

In some embodiments, the plurality of interlayer supports may comprise carbon nanotubes.

In some embodiments, the plurality of interlayer supports may comprise electrospun fibers.

In some embodiments, the plurality of interlayer supports may be disposed on an area of the upper surface of the support substrate layer ranging from about 5% to about 50% of the total area of the upper surface of the support substrate layer.

In some embodiments, the plurality of interlayers supports may be functionalized.

In some embodiments, the plurality of interlayer supports may be disposed on an area of the upper surface of the support substrate layer ranging from about 40% to about 45% of the total area of the upper surface of the support substrate layer.

In some embodiments, a two-dimensional membrane layered structure may comprise a support substrate layer having a plurality of substrate passages configured to allow fluid to flow therethrough, a two-dimensional membrane layer disposed on an upper surface of the support substrate layer, and a plurality of grooves formed on the upper surface of the support substrate layer. The two-dimensional membrane layer may have a plurality of pores configured to allow fluid to flow therethrough. The plurality of pores may comprise a first portion of pores that overlap with the plurality of substrate passages and a second portion of pores that do not overlap with the plurality of substrate passages. The plurality of grooves may be configured to form a plurality of flow channels that allow permeate to flow through the second portion of pores to the plurality of substrate channels.

In some embodiments, the plurality of grooves may be formed on the upper surface of the support substrate layer in a lattice pattern.

In some embodiments, the plurality of grooves may comprise a width of about 10 nanometers to about 1000 nanometers.

In some embodiments, the plurality of grooves may be functionalized.

In some embodiments, a method of increasing pore utilization in a two-dimensional membrane layered structure may comprise providing a substrate support layer having a plurality of substrate passages configured to allow fluid to flow therethrough, disposing a plurality of interlayer supports on an upper surface of the substrate support layer, and disposing a two-dimensional membrane layer having a plurality of pores configured to allow fluid to flow therethrough on the upper surface of the substrate support layer having the plurality of interlayer supports. The plurality of pores may comprise a first portion of pores that overlap with the plurality of substrate passages and a second portion of pores that do not overlap with the plurality of substrate passages. The plurality of interlayer supports may form a plurality of flow passages. The plurality of flow passages may be configured to allow fluid to flow through the second portion of pores to the plurality of substrate passages.

In some embodiments, the plurality of interlayer supports may comprise carbon nanotubes and the carbon nanotubes may be disposed on the upper surface of the support substrate layer via spray-coating.

In some embodiments, a method for increasing pore utilization in a two-dimensional membrane layered structure may comprise providing a substrate support layer having a plurality of substrate passages configured to allow fluid to flow therethrough, forming a plurality of grooves on an upper surface of the substrate support layer, and disposing a two-dimensional membrane layer having a plurality of pores configured to allow fluid to flow therethrough on the upper surface of the substrate support layer having the plurality of grooves. The plurality of pores may comprise a first portion of pores that overlap with the plurality of substrate passages and a second portion of pores that do not overlap with the plurality of substrate passages. The plurality of grooves may form a plurality of flow passages. The plurality of flow passages may be configured to allow fluid to flow through the second portion of pores to the plurality of substrate passages.

In some embodiments, the plurality of grooves may be formed in a lattice pattern.

In some embodiments, a two-dimensional membrane layered structure may comprise a support substrate layer having a plurality of substrate passages configured to allow fluid to flow therethrough, and a two-dimensional membrane layer disposed on an upper surface of the support substrate layer. The two-dimensional membrane layer may have a plurality of pores configured to allow fluid to flow therethrough. The plurality of pores may comprise a first portion of pores that overlap with the plurality of substrate passages and a second portion of pores that do not overlap with the plurality of substrate passages. The two-dimensional membrane layered structure may further comprise a flow passage means for allowing fluid to flow through the second portion of pores to the plurality of substrate passages to increase overall pore utilization of the two-dimensional membrane layer.

DETAILED DESCRIPTION

Some embodiments relate to a two-dimensional membrane layered structure having a plurality of flow passages formed between a two-dimensional membrane layer and a support substrate layer. The flow passages provide an increase in pore utilization by allowing fluid to flow through pores in the two-dimensional membrane layer that do not overlap with passages present in the support substrate. With the flow passages, fluid may flow from the non-overlapping pores through the flow passages to a nearby support substrate passage. In some embodiments, the flow passages may be formed by interlayer supports laterally disposed on an upper surface of the support substrate layer and/or by grooves laterally formed on the upper surface of the support substrate layer. In addition to increasing overall pore utilization of the membrane layer and total flow through the membrane structure, the flow passages may also provide sufficient support to the two-dimensional membrane without adding undesirable strain to the membrane layer.

Figure 1:
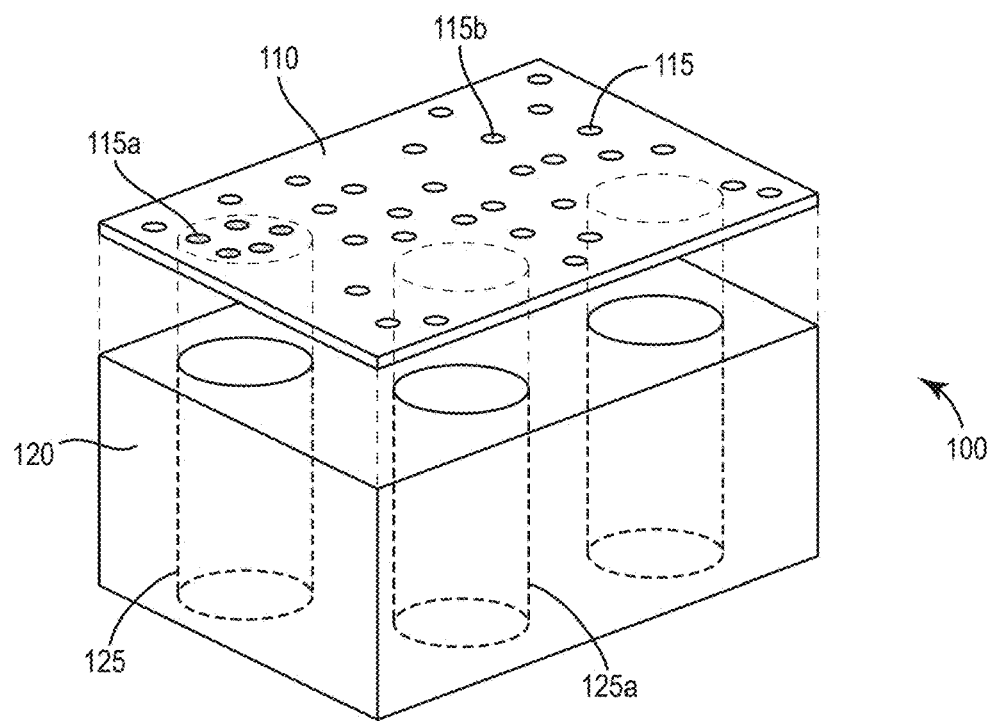
FIG. 1 is a perspective view of a two-dimensional membrane layered structure according to one embodiment.

FIG. 1 shows a perspective view of a two-dimensional membrane layered structure 100. The two-dimensional membrane layered structure 100 may include a two-dimensional membrane layer 110 having a plurality of pores 115, and a support substrate layer 120 having a plurality of substrate passages 125 that extend along a thickness of the support substrate layer 120.

The two-dimensional membrane layer 110 may be a single-layer two-dimensional material or a stacked two-dimensional material. Most generally, a single-layer two dimensional material is atomically thin, having an extended planar structure and a thickness on the nanometer scale. Single-layer two-dimensional materials generally exhibit strong in-plane chemical bonding relative to the weak coupling present between layers when such layers are stacked. Examples of single-layer two-dimensional materials include metal chalcogenides (e.g., transition metal dichalcogenides), transition metal oxides, boron nitride (e.g., hexagonal boron nitride), graphene, silicone, germanene, carbon nanomembranes (CNM), and molybdenum disulfide. Stacked two-dimensional materials may include a few layers (e.g., about 20 or less) of a single-layer two-dimensional material or various combinations of single-layer two-dimensional materials. In some embodiments, the two-dimensional membrane layer 110 may be a graphene or graphene-based two-dimensional material as a single-layer two-dimensional material or a stacked two-dimensional material.

The support substrate layer 120 may include any appropriate planar-type substrate. In some embodiments, the support substrate layer 120 may be made from ceramic porous materials, such as silica, silicon, silicon nitride, and combinations thereof. In some embodiments, he support substrate layer 120 may be made from a polymer material, such as track-etched polymers, expanded polymers, patterned polymers, non-woven polymers, and combinations thereof. The support substrate layer 120 may include a polymer selected from the group consisting of polysulfones, polyurethane, polymethylmethacrylate (PMMA), polyethylene glycol (PEG), polylactic-co-glycolic acid (PLGA), PLA, PGA, polyamides (such as nylon-6,6, supramid and nylamid), polyimides, polypropylene, polyethersulfones (PES), polyvinylidine fluoride (PVDF), cellulose acetate, polyethylene, polypropylene, polycarbonate, polytetrafluoroethylene (PTFE) (such as Teflon), polyvinylchloride (PVC), polyether ether ketone (PEEK), mixtures and block co-polymers of any of these, and combinations and/or mixtures thereof. In some embodiments, the polymers may be biocompatible, bioinert and/or medical grade materials. In some embodiments, the support substrate layer 120 may be a track-etched polycarbonate (TEPC) membrane. In other embodiments, the support substrate layer 120 may be a membrane formed by silicon nitride, track-etched polyimide, track-etched polyester, track-etched SiN, nanoporous silicon, nanoporous silicon nitride, an electrospun membrane, and/or a PVDF membrane. In some embodiments, the substrate passages 125 may be formed randomly or in a patterned manner.

As shown in FIG. 1, when disposing the two-dimensional membrane layer 110 on the support substrate 120, only a certain percentage of pores 115 overlap with the substrate passages 125. For example, a first portion of pores 115a overlap with, or are in fluid communication with, the support substrate passages 125. The first portion of pores 115a contributes to overall pore utilization because they allow fluid to flow through to the substrate passages 125. On the other hand, a second portion of pores 115b do not overlap with, or fail to be in fluid communication with, the support substrate passages 125. Thus, the second portion of pores 115b does not contribute to overall pore utilization because fluid cannot flow from these pores into the support substrate passages 125. Moreover, as further shown in FIG. 1, in some cases, a support substrate passage 125a may fail to be in fluid communication with any of the pores 115. Thus, this blocked support substrate passage 125a receives no fluid flow, thereby decreasing the overall utilization of the support substrate passages 125.

Figure 2:
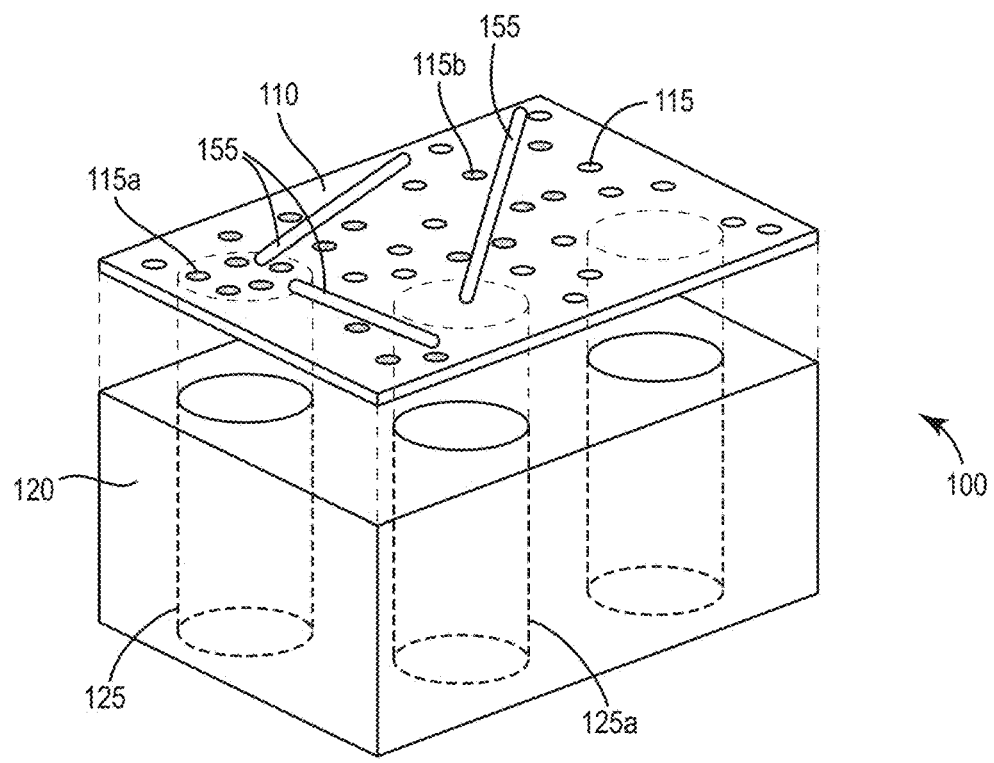
FIG. 2 is a perspective of the two-dimensional membrane layered structure of FIG. 1 having fluid flow passages.

FIG. 2 illustrates a perspective view of the two-dimensional membrane layered structure 100 having a plurality of flow passages 155 disposed between the two-dimensional membrane layer 110 and the support substrate layer 120. As shown in FIG. 2, the flow passages 155 provide a means for the second portion of pores 115b to be utilized by providing a flow path for fluid to flow from a respective pore 115b to a nearby substrate passage 125. In some embodiments, the flow passages 155 may also provide a flow path from the second portion of pores 115b to the blocked support substrate passage 125a such that fluid may flow through the blocked support substrate passage 125a. Thus, the integration of the flow passages 155 provide for an increase in the overall pore utilization of the two-dimensional membrane layer 110 and a means for increased fluid flow through the support substrate layer 120.

Figure 3:
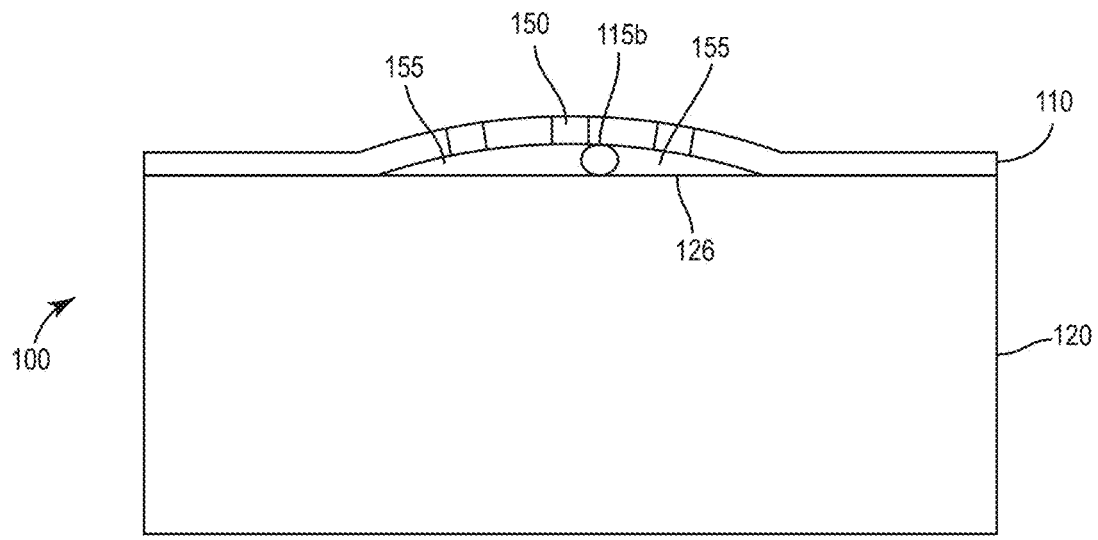
FIG. 3 is a cross-sectional view of the two-dimensional membrane layered structure having the flow passages of FIG. 2 according to a first embodiment.

FIG. 3 shows a cross-sectional view of the two-dimensional membrane layered structure 100 having flow passages 155 formed therein in accordance with a first embodiment. As shown in FIG. 3, a plurality of interlayer supports 150 may be disposed laterally on an upper surface 126 of the support substrate layer 120. The two-dimensional membrane layer 110 is then disposed onto the upper surface 126 of the support substrate layer 120 having the interlayer supports 150 disposed thereon. When layered, the interlayer supports 150 support the two-dimensional membrane layer 110 while pushing the two-dimensional membrane layer 110 upward from the support substrate layer 120 to form the flow passages 155 that allow fluid to flow through the pores 115b.

Figure 5:
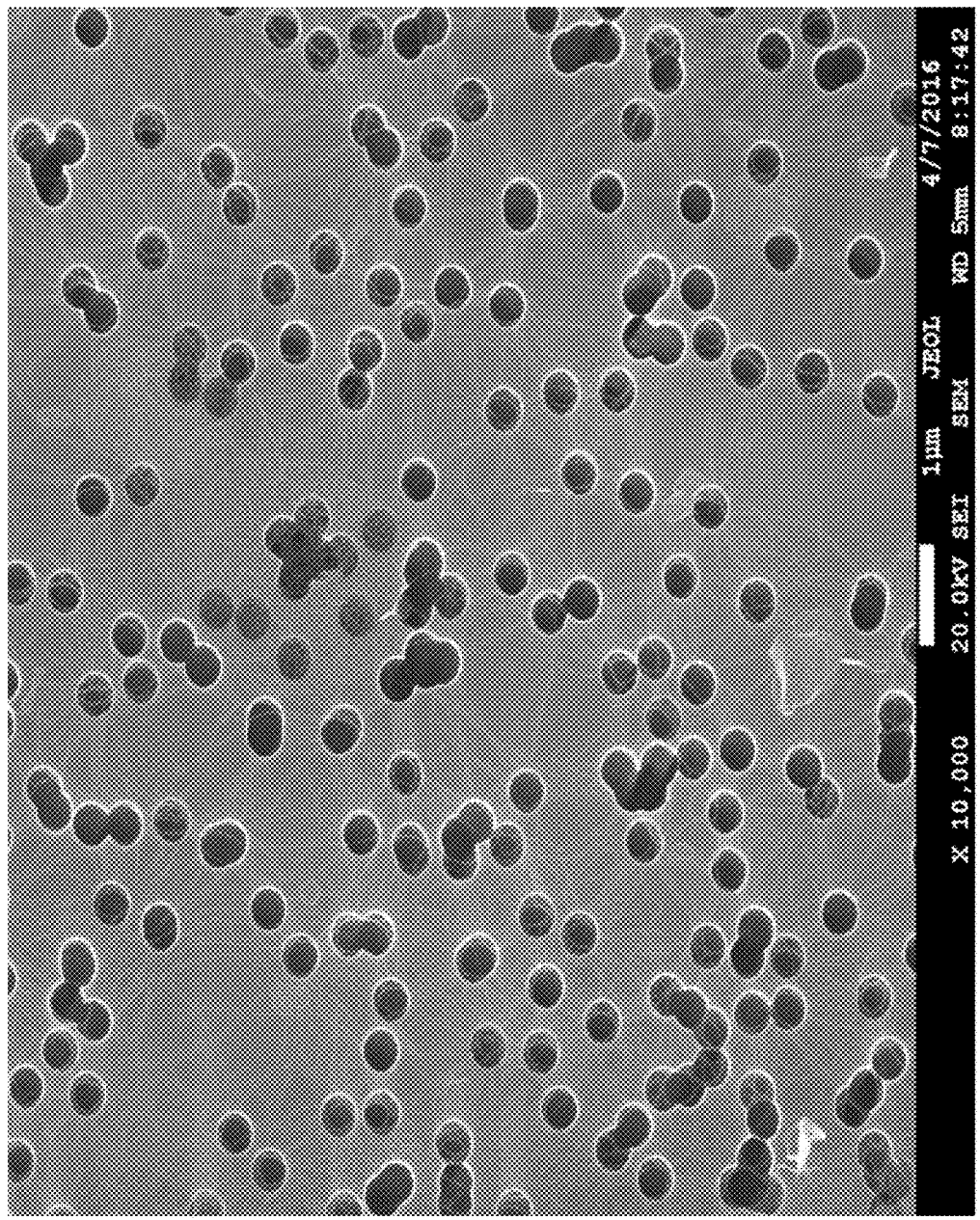
FIG. 5 is a scanning electron microscope (SEM) micrograph of a support substrate layer having interlayer supports to form fluid flow passages.
Figure 6:
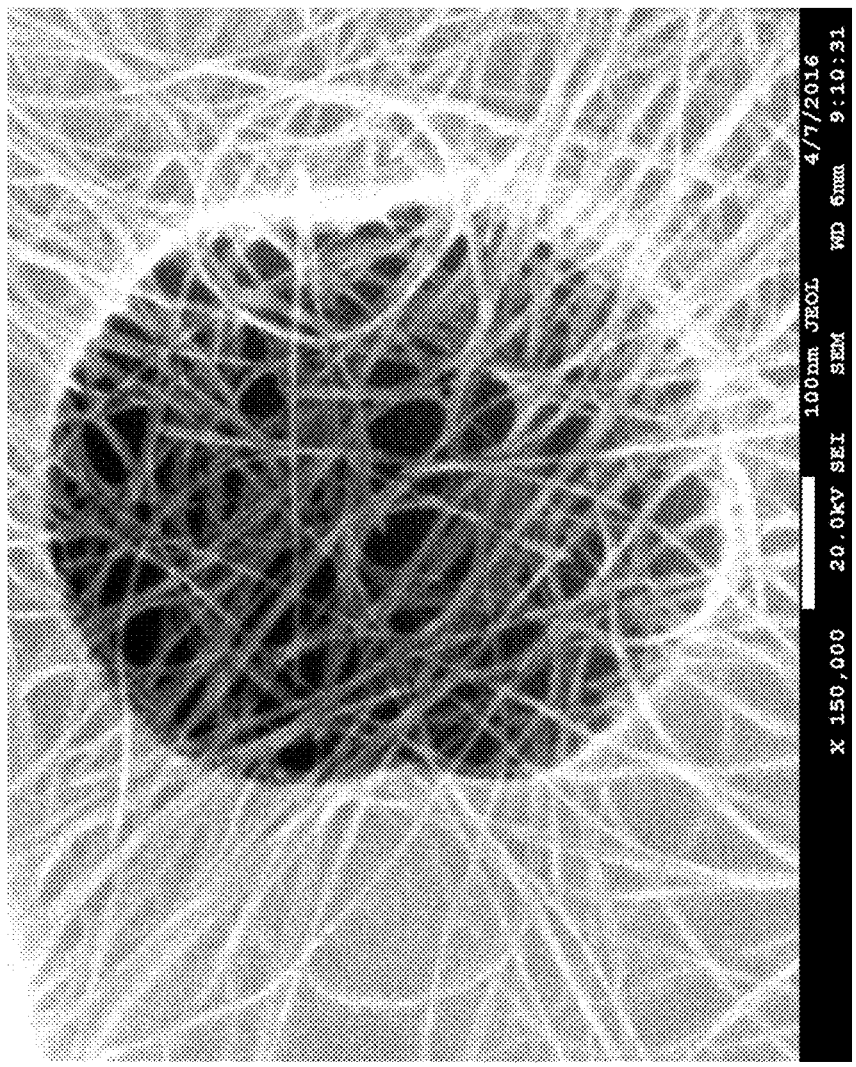
FIG. 6 is a detailed SEM micrograph of the support substrate layer of FIG. 5.

The interlayer supports 150 may take numerous forms. For example, in some embodiments, the interlayer supports 150 may be carbon nanotubes. For example, FIGS. 5 and 6 show interlayer supports in the form of carbon nanotubes spray-coated onto an upper surface of a support substrate layer in the form of a track-etched polyimide layer before the two-dimensional membrane layer is disposed onto the support substrate layer. As shown the figures, the carbon nanotubes are disposed onto the upper surface of the support substrate layer so as to extend laterally across the upper surface to provide access for fluid flow to the substrate passages. In some embodiments, the carbon nanotubes may be single-walled or multi-walled.

In other embodiments, the interlayer supports 150 may be electrospun fibers. In yet other embodiments, the interlayer supports 150 may be nanorods, nanoparticles (e.g., oxide nanoparticles, octadecyltrichlorosilane nanoparticles), fullerenes, collagen, keratin, aromatic amino acids, polyethylene glycol, lithium niobate particles, decorated nano-dots, nanowires, nanostrands, lacey carbon material, proteins, polymers (e.g., hygroscopic polymer, thin polymer, amorphous polymer), hydrogels, self-assembled monolayers, allotropes, nanocrystals of 4-dimethylamino-N-methyl-4-stilbazolium tosylate, crystalline polytetrafluoroethylene, or combinations thereof. In some embodiments, the density of the interlayer supports 150 may comprise about 5% to about 50% of the total area of the upper surface 126 of the substrate support layer 120 to provide a sufficient pore utilization increase to the composite 100, while at the same time minimizing a decrease in mechanical support of the two-dimensional membrane layer 110. In some embodiments, the density of the interlayer supports 150 comprises 40 to 45% of the total area of the upper surface 126 of the support substrate layer 120.

The interlayer supports 150 may be applied to the upper surface 126 of the support substrate layer 120 in any appropriate manner. For example, the some embodiments, the interlayer supports 150 may be carbon nanotubes that may be spray-coated in random orientations onto the upper surface 126 of the support substrate layer 120. The spray-coating may be controlled such that the density of the carbon nanotubes applied to the upper surface 126 may be fine-tuned. Other methods of disposing the interlayer supports 150 onto the upper surface 126 of the support substrate layer 120 may include, but are not limited to, electrostatic deposition, drop casting, spin-coating, sputtering, lithography, ion beam induced deposition, atomic layer deposition, or electron beam induced deposition. Additional methods include the application of electrospun fibers by an electric field, the acceleration of nanoparticles by a potential, or the use of an ion beam to irradiate material present on the upper surface 126 to form raised structures on the upper surface 126 of the support substrate layer 120.

Figure 4:
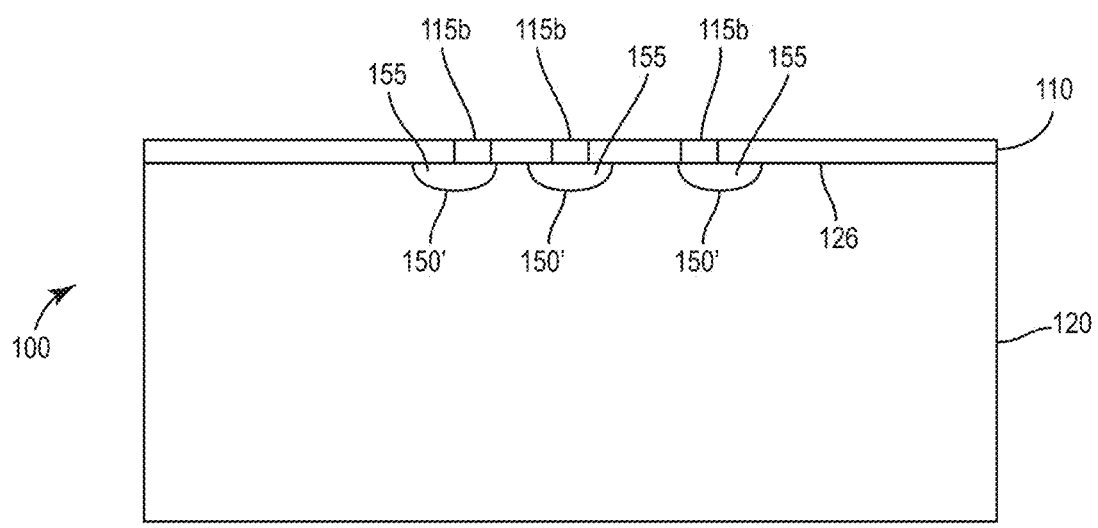
FIG. 4 is a cross-sectional view of the two-dimensional membrane layered structure having the flow passages of FIG. 2 according to a second embodiment.

FIG. 4 shows a cross-sectional view of the two-dimensional membrane layered structure 100 having flow passages 155 formed therein in accordance with a second embodiment. As shown in FIG. 4, before transferring the two-dimensional membrane layer 110 onto the support substrate layer 120, a plurality of grooves 150' are laterally formed onto the upper surface 126 of the support substrate layer 120 to form the flow channels 155. As such, fluid may flow through the pores 115b to the support substrate channels 125, thereby increasing the overall pore utilization of the two-dimensional membrane layer 110.

The plurality of grooves 150' may be formed into the upper surface 126 of the support substrate layer 125 by any appropriate means. For example, in some embodiments, the grooves 150' may be formed by etching the upper surface 126. In other embodiments, the grooves 150' may be formed by focused ion beam milling, lithography methods (e.g., optical, electron beam lithography, extreme UV lithography) on resists followed by suitable etching (e.g., reactive ion etching), block copolymer mask focused on columnar and aligned structures followed by suitable etching, laser ablation, nanoimprint, scanning probe lithography, shadowmask deposition followed by suitable etching, or sparse aperture masking methods.

In some embodiments, the grooves 150' may be formed in a regular, structured pattern, such as a lattice-like pattern, or in a random pattern. In addition, the grooves 150' may be formed to have a depth and a width of about 1 nm to about 5 µm. In some embodiments, the depth and width may range from about 10 nm to about 1000 nm. In other embodiments, the depth and width of the grooves 150' may range from about 50 nm to about 250 nm. In certain embodiments, the density of the grooves 150' may comprise up to 50 to 75% of the total area of the upper surface 126 of the support substrate layer 120.

Some embodiments, such as described above, allow for the formation of fluid flow passages in a two-dimensional membrane layered structure. In some embodiments, the flow passages may be formed by interlayer supports disposed on an upper surface of the support substrate layer. In other embodiments, the flow passages may be formed by grooves provided on the upper surface of the support substrate layer. In yet other embodiments, the flow passages may be formed both by interlayer supports disposed on the upper surface of the support substrate layer and grooves provided on the upper surface of the support substrate layer. The fluid flow passages may be formed between the two-dimensional support layer and the support substrate layer such that an increase in the amount of pores that allow fluid to flow to passages in the support substrate layer may be realized. Thus, the flow passages may result in an increase in overall pore utilization in the layered structure without resulting in a loss of mechanical support provided to the two-dimensional membrane.

The two-dimensional membrane layered structures described herein have broad application, including in water filtration, immune-isolation, (i.e., protecting substances from an immune reaction), timed drug release (e.g., sustained or delayed release), hemodialysis, and hemofiltration. Some embodiments described herein comprise a method of water filtration, water desalination, water purification, immune-isolation, timed drug release, hemodialysis, or hemofiltration, where the method comprises exposing a two-dimensional membrane layered structure to an environmental stimulus, and wherein the two-dimensional membrane layered structure comprises a two-dimensional membrane layer having a plurality of pores (e.g., a porous graphene-based material) and a support substrate layer having a plurality of substrate passages.

Some embodiments include methods of filtering water comprising passing water through a two-dimensional membrane layered structure. Some embodiments include desalinating or purifying water comprising passing water through a two-dimensional membrane layered structure. The water can be passed through the two-dimensional membrane layered structure by any known means, such as by diffusion or gravity filtration, or with applied pressure (e.g., applied with a pump or via osmotic pressure).

Some embodiments include methods of selectively separating or isolating substances in a biological environment, wherein the two-dimensional membrane layered structure separates or isolates biological substances based on characteristics of the substance, such as size. Such methods can be useful in the context of disease treatment, such as in the treatment of diabetes. In some embodiments, biological substances below a certain size threshold can migrate across the two-dimensional membrane layered structure. In some embodiments, even biological substances below the size threshold are excluded from migrating across the two-dimensional membrane layered structure due to functionalization of the plurality of pores, the plurality of substrate passages, the plurality of interlayer supports and/or the plurality of grooves.

In some embodiments, the plurality of pores, or at least a portion thereof, is functionalized. In some embodiments, the plurality of substrate passages, or at least a portion thereof, is functionalized, for instance by attaching or embedding a functional group. In some embodiments, the plurality of interlayer supports and/or the plurality of grooves, or at least a portion thereof, is functionalized, for instance by attaching or embedding a functional group. In some embodiments, the functionalization moieties are trapped between two layers, but are not restricted to a single position in the flow passages (i.e., they are mobile within the flow passages, but are inhibited from traversing the layers, e.g., based the size of the pores in the two-dimensional membrane layer). In some embodiments, functionalization comprises surface charges (e.g., sulfonates) attached to the pores, substrate passages, interlayer supports, and/or grooves. Without being bound by theory, it is believed that surface charges can impact which molecules and/or ions can traverse the two-dimensional membrane layered structure. In some embodiments, functionalization comprises specific binding sites attached to the pores, substrate passages, interlayer supports, and/or grooves. In some embodiments, functionalization comprises proteins or peptides attached to the pores, substrate passages, interlayer supports, and/or grooves. In some embodiments, functionalization comprises antibodies and/or antigens (e.g., IgG-binding antigens) attached to the pores, substrate passages, interlayer supports, and/or grooves. In some embodiments, functionalization comprises adsorptive substances attached to the pores, substrate passages, interlayer supports, and/or grooves. In some embodiments, functionalization involves catalytic and/or regenerative substances or groups. In some embodiments, functionalization comprises a negatively or partially negatively charged group (e.g., oxygen) attached to the pores, substrate passages, interlayer supports, and/or grooves. In some embodiments, functionalization comprises a positively or partially positively charged group attached to the pores, substrate passages, interlayer supports, and/or grooves.

In some embodiments, functionalizing the pores, substrate passages, interlayer supports, and/or grooves functions to: restrict contaminants from traversing the two-dimensional membrane layered structure; act as a disposable filter, capture, or diagnostic tool; increase biocompatibility (e.g., when polyethylene glycol is used for functionalization); increase filtration efficiency; position the interlayer supports (e.g., interlayer supports can be positioned near the pores via affinity-based functionalization in the pores; additional spacers can be positioned in interlaminar areas); increase selectivity at or near the pores or in asymmetric two-dimensional membrane layered structure; and/or protect interlayer supports (e.g., from the external environment or from a particular vulnerability such as degradation).

Some embodiments have been described in detail with particular reference to preferred embodiments thereof, but it will be understood by those skilled in the art that variations and modifications can be effected within the spirit and scope of the claims.

What is claimed is:

1. A two-dimensional membrane layered structure comprising:
   a support substrate layer having a plurality of substrate passages configured to allow fluid to flow therethrough;
   a two-dimensional membrane layer disposed on an upper surface of the support substrate layer, the two-dimensional membrane layer having a plurality of pores configured to allow fluid to flow therethrough, the plurality of pores comprising a first portion of pores that overlap with the plurality of substrate passages and a second portion of pores that do not overlap with the plurality of substrate passages; and a plurality of flow passages disposed between the support substrate layer and the two-dimensional membrane layer, the plurality of flow passages being configured to allow fluid to flow through the second portion of pores to the plurality of substrate passages.

2. The two-dimensional membrane layered structure of claim 1, further comprising a plurality of interlayer supports disposed on an upper surface of the support substrate layer, wherein the plurality of interlayer supports form the plurality of flow passages.

3. The two-dimensional membrane layered structure of claim 1, further comprising a plurality of grooves formed on an upper surface of the support substrate layer, wherein the plurality of grooves form the plurality of flow passages.

4. The two-dimensional membrane layered structure of claim 1, further comprising a plurality of interlayer supports disposed on an upper surface of the support substrate layer and a plurality of grooves formed on an upper surface of the support substrate layer, wherein the plurality of interlayer supports and the plurality of grooves form the plurality of flow passages.

5. A two-dimensional membrane layered structure comprising:
a support substrate layer having a plurality of substrate passages configured to allow fluid to flow therethrough;
a two-dimensional membrane layer disposed on an upper surface of the support substrate layer, the two-dimensional membrane layer having a plurality of pores configured to allow fluid to flow therethrough, and the plurality of pores comprising a first portion of pores that overlap with the plurality of substrate passages and a second portion of pores that do not overlap with the plurality of substrate passages; and
a plurality of interlayer supports disposed on the upper surface of the support substrate layer,
wherein the plurality of interlayer supports is configured to form a plurality of flow passages that allow fluid to flow through the second portion of pores to the plurality of substrate passages.

6. The two-dimensional membrane layered structure of claim 5, wherein the plurality of interlayer supports comprises carbon nanotubes.

7. The two-dimensional membrane layered structure of claim 5, wherein the plurality of interlayer supports comprises electrospun fibers.

8. The two-dimensional membrane layered structure of claim 5, wherein the plurality of interlayer supports is disposed on an area of the upper surface of the support substrate layer ranging from about 5% to about 50% of the total area of the upper surface of the support substrate layer.

9. The two-dimensional membrane layered structure of claim 5, wherein the plurality of interlayer supports is functionalized.

10. The two-dimensional membrane layered structure of claim 5, wherein the plurality of interlayer supports is disposed on an area of the upper surface of the support substrate layer ranging from about 40% to about 45% of the total area of the upper surface of the support substrate layer.

11. A two-dimensional membrane layered structure comprising:
a support substrate layer having a plurality of substrate passages configured to allow fluid to flow therethrough;
a two-dimensional membrane layer disposed on an upper surface of the support substrate layer, the two-dimensional membrane layer having a plurality of pores configured to allow fluid to flow therethrough, and the plurality of pores comprising a first portion of pores that overlap with the plurality of substrate passages and a second portion of pores that do not overlap with the plurality of substrate passages; and
a plurality of grooves formed on the upper surface of the support substrate layer,
wherein the plurality of grooves is configured to form a plurality of flow channels that allow permeate to flow through the second portion of pores to the plurality of substrate channels.

12. The two-dimensional membrane layered structure of claim 11, wherein the plurality of grooves is formed on the upper surface of the support substrate layer in a lattice pattern.

13. The two-dimensional membrane layered structure of claim 11, wherein the plurality of grooves comprises a width of about 10 nanometers to about 1000 nanometers.

14. The two-dimensional membrane layered structure of claim 11, wherein the plurality of grooves is functionalized.

15. A two-dimensional membrane layered structure comprising:
a support substrate layer having a plurality of substrate passages configured to allow fluid to flow therethrough;
a two-dimensional membrane layer disposed on an upper surface of the support substrate layer, the two-dimensional membrane layer having a plurality of pores configured to allow fluid to flow therethrough, the plurality of pores comprising a first portion of pores that overlap with the plurality of substrate passages and a second portion of pores that do not overlap with the plurality of substrate passages; and
a flow passage means for allowing fluid to flow through the second portion of pores to the plurality of substrate passages to increase overall pore utilization of the two-dimensional membrane layer.

* * * * *